(12) United States Patent
Soletti et al.

(10) Patent No.: US 10,239,071 B2
(45) Date of Patent: Mar. 26, 2019

(54) GRAFT DEVICES AND METHODS OF USE

(71) Applicant: Neograft Technologies, Inc., Taunton, MA (US)

(72) Inventors: Lorenzo Soletti, Pittsburgh, PA (US); Mohammed S. El-Kurdi, Pittsburgh, PA (US); Jon McGrath, Duxbury, MA (US); Andrew Ziegler, Arlington, MA (US); J. Christopher Flaherty, Auburndale, FL (US); William R. Wagner, Wexford, PA (US); David Vorp, Pittsburgh, PA (US)

(73) Assignees: Neograft Technologies, Inc., Taunton, MA (US); University Of Pittsburgh—of the Commonwealth System of Higher Education, Pittsburgh, PA (US)

( * ) Notice: Subject to any disclaimer, the term of this patent is extended or adjusted under 35 U.S.C. 154(b) by 170 days.

(21) Appl. No.: 15/228,339

(22) Filed: Aug. 4, 2016

(65) Prior Publication Data

US 2017/0043360 A1    Feb. 16, 2017

Related U.S. Application Data

(63) Continuation of application No. 13/811,206, filed as application No. PCT/US2011/044510 on Jul. 19, 2011, now Pat. No. 9,445,874.

(Continued)

(51) Int. Cl.
*B05B 5/12* (2006.01)
*B05B 5/025* (2006.01)
(Continued)

(52) U.S. Cl.
CPC .............. *B05B 5/12* (2013.01); *A61B 90/00* (2016.02); *A61F 2/022* (2013.01); *A61F 2/04* (2013.01);
(Continued)

(58) Field of Classification Search
CPC .. A61L 27/3625; D01D 5/0084; D01D 13/02; A61B 90/00; A61F 2/022;
(Continued)

(56) References Cited

U.S. PATENT DOCUMENTS 4,323,525 A    4/1982 Bornat
4,552,707 A    11/1985 How
(Continued)

FOREIGN PATENT DOCUMENTS

CA    2677033 A1    8/2008
CN    1491728 A     4/2004
(Continued)

OTHER PUBLICATIONS

Alcocer, et al. Mutual exclusion of apoptosis and hsp70 in human vein intimal hyperplasia in vitro. J Surg Res. 2001;96(1): 75-80.
(Continued)

*Primary Examiner* — Catherine B Kuhlman
*Assistant Examiner* — Joshua D Lannu
(74) *Attorney, Agent, or Firm* — Wilson Sonsini Goodrich & Rosati

(57) ABSTRACT

A cartridge device is provided for applying a fiber matrix to a tubular member such as a saphenous vein graft. The cartridge includes a housing, a tubular member holder, a rotational drive, and a polymer delivery assembly. The housing defines a chamber which surrounds the tubular member holder. The rotational drive rotates the tubular member during the fiber application process.

20 Claims, 8 Drawing Sheets

Related U.S. Application Data

(60) Provisional application No. 61/365,612, filed on Jul. 19, 2010.

(51) Int. Cl.

| | | |
|---|---|---|
| *A61F 2/07* | (2013.01) | |
| *A61F 2/02* | (2006.01) | |
| *A61F 2/04* | (2013.01) | |
| *A61F 2/06* | (2013.01) | |
| *A61L 27/36* | (2006.01) | |
| *D01D 5/00* | (2006.01) | |
| *D01D 13/02* | (2006.01) | |
| *A61B 90/00* | (2016.01) | |

(52) U.S. Cl.
CPC .............. *A61F 2/06* (2013.01); *A61F 2/07* (2013.01); *A61L 27/3625* (2013.01); *B05B 5/0255* (2013.01); *D01D 5/0084* (2013.01); *D01D 13/02* (2013.01); *A61F 2002/043* (2013.01); *A61F 2002/046* (2013.01); *A61F 2002/047* (2013.01); *A61F 2002/048* (2013.01); *A61F 2240/001* (2013.01)

(58) Field of Classification Search
CPC .......... A61F 2240/001; A61F 2002/048; A61F 2002/047; A61F 2002/043; A61F 2/07; A61F 2/06; A61F 2/04; A61F 2002/046; B05B 5/0255; B05B 5/12
See application file for complete search history.

(56) References Cited

U.S. PATENT DOCUMENTS

| | | |
|---|---|---|
| 4,689,186 A | 8/1987 | Bomat |
| 4,738,740 A | 4/1988 | Pinchuk |
| 4,798,606 A | 1/1989 | Pinchuk |
| 4,955,899 A | 9/1990 | Della Corma et al. |
| 5,024,789 A | 6/1991 | Berry |
| 5,662,700 A | 9/1997 | Lazarus |
| 5,813,167 A | 9/1998 | Hoshino et al. |
| 6,030,371 A | 2/2000 | Pursley |
| 6,036,702 A | 3/2000 | Bachinski et al. |
| 6,036,724 A | 3/2000 | Lentz et al. |
| 6,165,212 A | 12/2000 | Dereume et al. |
| 6,187,038 B1 | 2/2001 | Sullivan et al. |
| 6,296,863 B1 | 10/2001 | Trogolo et al. |
| 6,440,163 B1 | 8/2002 | Swanson et al. |
| 6,599,323 B2 | 7/2003 | Melican et al. |
| 6,891,077 B2 | 5/2005 | Rothwell et al. |
| 7,033,388 B2 | 4/2006 | Zilla et al. |
| 7,037,332 B2 | 5/2006 | Kutryk et al. |
| 7,166,124 B2 | 1/2007 | Xie et al. |
| 7,192,440 B2 | 3/2007 | Anreas et al. |
| 7,326,237 B2 | 2/2008 | Depalma et al. |
| 7,374,774 B2 | 5/2008 | Bowlin et al. |
| 7,413,575 B2 | 8/2008 | Phaneuf et al. |
| 7,452,374 B2 | 11/2008 | Hain et al. |
| 7,531,503 B2 | 5/2009 | Atala et al. |
| 7,641,844 B2 | 1/2010 | Melsheimer |
| 7,759,099 B2 | 7/2010 | Wolf et al. |
| 7,759,120 B2 | 7/2010 | Wolf et al. |
| 7,794,219 B2 | 9/2010 | Dubson et al. |
| 7,833,267 B2 | 11/2010 | Flagle et al. |
| 7,901,446 B2 | 3/2011 | Flagle et al. |
| 7,905,826 B2 | 3/2011 | Case et al. |
| 7,922,761 B2 | 4/2011 | Shalev et al. |
| 7,998,188 B2 | 8/2011 | Zilla et al. |
| 8,057,537 B2 | 11/2011 | Zilla et al. |
| 8,076,529 B2 | 12/2011 | Ehrenreich et al. |
| 8,172,746 B2 | 5/2012 | Zilla et al. |
| 8,267,989 B2 | 9/2012 | Whirley et al. |
| 8,292,799 B2 | 10/2012 | Xu |
| 8,353,814 B2 | 1/2013 | Villafana et al. |
| 8,491,457 B2 | 7/2013 | Atala et al. |
| 2002/0042128 A1 | 4/2002 | Bowlin et al. |
| 2002/0123786 A1 | 9/2002 | Gittings et al. |
| 2003/0109887 A1 | 6/2003 | Galdonik et al. |
| 2004/0073294 A1 | 4/2004 | Diaz et al. |
| 2004/0094873 A1 | 5/2004 | Dubson et al. |
| 2004/0146546 A1 | 7/2004 | Gravett et al. |
| 2004/0171545 A1 | 9/2004 | Chaikof et al. |
| 2004/0219185 A1 | 11/2004 | Ringeisen |
| 2005/0187605 A1 | 8/2005 | Greenhalgh et al. |
| 2005/0203636 A1 | 9/2005 | McFetridge |
| 2006/0075963 A1* | 4/2006 | Nieponice .............. A61F 2/062 118/417 |
| 2006/0085063 A1 | 4/2006 | Shastri et al. |
| 2006/0129234 A1 | 6/2006 | Phaneuf et al. |
| 2006/0240061 A1 | 10/2006 | Atala et al. |
| 2006/0257447 A1 | 11/2006 | Hinds et al. |
| 2007/0087027 A1 | 1/2007 | Greenhalgh et al. |
| 2007/0173917 A1 | 7/2007 | Hayashi et al. |
| 2007/0239267 A1 | 10/2007 | Hendriks et al. |
| 2007/0269481 A1 | 11/2007 | Li et al. |
| 2008/0208323 A1 | 8/2008 | El-Kurdi et al. |
| 2009/0012607 A1 | 1/2009 | Kim et al. |
| 2009/0030580 A1 | 1/2009 | Tang et al. |
| 2009/0088828 A1 | 4/2009 | Shalev et al. |
| 2010/0160718 A1 | 6/2010 | Villafana et al. |
| 2010/0280598 A1 | 11/2010 | Fox |
| 2010/0331964 A1 | 12/2010 | Clerin et al. |
| 2011/0288628 A1 | 11/2011 | Noesner et al. |
| 2012/0116495 A1 | 5/2012 | Zilla et al. |
| 2014/0005470 A1 | 1/2014 | Soletti et al. |

FOREIGN PATENT DOCUMENTS

| | | |
|---|---|---|
| EP | 0095940 A2 | 12/1983 |
| EP | 0265176 A2 | 4/1988 |
| JP | H 1176278 A | 3/1999 |
| JP | 2003235880 A | 8/2003 |
| JP | 2004525272 A | 8/2004 |
| JP | 2006515186 A | 5/2006 |
| JP | 2006526658 A | 11/2006 |
| KR | 100595487 B1 | 7/2006 |
| WO | WO 98/32367 A2 | 7/1998 |
| WO | WO 2004/028583 A2 | 4/2004 |
| WO | WO 2006/044904 A2 | 4/2006 |
| WO | WO 2006/136817 A1 | 12/2006 |
| WO | WO 2007/003199 A1 | 1/2007 |
| WO | WO 2009/103012 A1 | 8/2009 |
| WO | WO 2010/042721 A1 | 4/2010 |
| WO | WO 2011/056705 A2 | 5/2011 |
| WO | WO 2011/082295 A2 | 7/2011 |
| WO | WO 2011/084559 A2 | 7/2011 |

OTHER PUBLICATIONS

Angelini, et al. Distention promotes platelet and leukocyte adhesion and reduces short-term patency in pig arteriovenous bypass grafts. J Thorac Cardiovasc Surg. 1990;99(3): 4339.

Annabi, et al. Differential regulation of matrix metalloproteinase activities in abdominal aortic aneurysms. J Vasc Surg. 2002;35(3): 539-46.

Asanuma, et al. Uniaxial strain upregulates matrix-degrading enzymes produced by human vascular smooth muscle cells. Am J Physiol Heart Circ Physiol. 2003;284(5): H1778-84.

Ayres, et al. Modulation of anisotropy in electrospun tissue-engineering scaffolds: Analysis of fiber alignment by the fast Fourier transform. Biomaterials 27 (2006) 5524-5534.

Bandyk, et al. The failing graft: An evolving concept. Semin Vasc Surg. 1993;6(2): 75-7.

Bassiouny, et al. Anastomotic intimal hyperplasia: Mechanical injury or flow induced. J Vasc Surg. 1992;15(4): 708-16; discussion 716-7.

Bassiouny, et al. Low flow enhances platelet activation after acute experimental arterial injury. J Vasc Surg. 1998;27(5): 910-8.

Ben-Gal, et al. Expandable external support device to improve saphenous vein graft patency after CABG. J Cardiothorac Surg 2013;8:122.

(56) References Cited

OTHER PUBLICATIONS

Berkowitz, et al. Reversed vein graft stenosis: Early diagnosis and management. J Vasc Surg. 1992;15(1): 130-41; discussion 141-2.
Bornstein, P. Diversity of function is inherent in matricellular proteins: An appraisal of thrombospondin 1. J Cell Biol. 1995;130(3): 503-6.
Brant, et al. Measurement in vitro of pulsatile arterial diameter using a helium-neon laser. J Appl Physiol. 1987;62(2): 679-83.
Bunt, TJ. Synthetic vascular graft infections. I. Graft infections. Surgery. 1983;93(6): 733-46.
Cabrera-Fischer, et al. Reduced elastic mismatch achieved by interposing vein cuff in expanded polytetrafluoroethylene femoral bypass decreases intimal hyperplasia. Artif Organs. 2005;29(2): 122-30.
Cagiannos, et al. Rapamycin-coated expanded polytetrafluoroethylene bypass grafts exhibit decreased anastomotic neointimal hyperplasia in a porcine model. J Vasc Surg. 2005;42(5): 980-8.
Campbell, et al. Arterial smooth muscle. A multifunctional mesenchymal cell. Arch Pathol Lab Med. 1988;112(10): 977-86.
Campbell, et al. Vein grafts for arterial repair: Their success and reasons for failure. Ann R Coll Surg Engl. 1981;63(4): 257-60.
Chakrabarty, S. Fibrin solubilizing properties of certain anionic and cationic detergents. Thrombosis research 55.4 (1989): 511-519.
Cho, et al. Matrix metalloproteinase-9 is necessary for the regulation of smooth muscle cell replication and migration after arterial injury. Circ Res. 2002;91(9): 845-51.
Courtney, et al. Design and analysis of tissue engineering scaffolds that mimic soft tissue mechanical anisotropy. Biomaterials. 2006, 27: 3631-3638.
Davies, et al. Pre-bypass morphological changes in vein grafts. Eur J Vasc Surg. 1993;7(6): 642-7.
Davies, et al. Prevention of malalignment during non-reversed femorodistal bypass. Ann R Coll Surg Engl. 1992;74(6): 434-5.
Deitzel, et al. Controlled deposition of electrospun poly(ethylene oxide) fibers. Polymer. 2001, 42: 8163-8170.
Deitzel, et al. The effect of processing variable on the morphology of electrospun nanofibers and textiles. Polymer 42 (2001): 261-272.
Dethlefsen, et al. Comparison of the effects of mechanical stimulation on venous and arterial smooth muscle cells in vitro. J Vasc Res. 1996;33(5): 40513.
Dobrin, et al. Mechanical factors predisposing to intimal hyperplasia and medial thickening in autogenous vein grafts. Surgery. 1989;105(3): 393-400.
Ducasse, et al. Interposition vein cuff and intimal hyperplasia: An experimental study. Eur J Vasc Endovasc Surg. 2004;27(6): 617-21.
Edwards, et al. Primary graft infections. J Vasc Surg. 1987;6(3): 235-9.
Francis, et al. Release of platelet-derived growth factor activity from pig venous arterial grafts. J Thorac Cardiovasc Surg. 1994;108(3): 540-8.
Fuchs, et al. Postoperative changes in autologous vein grafts. Ann Surg. 1978;188(1): 1-15.
Fujimoto, et al. An elastic, biodegradable cardiac patch induces contractile smooth muscle and improves cardiac remodeling and function in subacute myocardial infarction. J Am Coll Cardiol. 2007;49(23): 2292-300.
Fujimoto, et al. In vivo evaluation of a porous, elastic, biodegradable patch for reconstructive cardiac procedures. Ann Thorac Surg. 2007;83(2): 648-54.
Galis, et al. Cytokine-stimulated human vascular smooth muscle cells synthesize a complement of enzymes required for extracellular matrix digestion. Circulation Research (Online). 1994;75(1): 181-9.
Garanich, et al. Shear stress inhibits smooth muscle cell migration via nitric oxide-mediated downregulation of matrix metalloproteinase-2 activity. Am J Physiol Heart Circ Physiol. 2005;288(5): H2244-52.
George, et al. Adenovirus-mediated gene transfer of the human T1MP-1 gene inhibits smooth muscle cell migration and neointimal formation in human saphenous vein. Hum Gene Then 1998;9(6): 867-77.

George, et al. Gene transfer of tissue inhibitor of metalloproteinase-2 inhibits metalloproteinase activity and neointima formation in human saphenous veins. Gene Ther. 1998;5(11): 1552-60.
George, et al. Surgical preparative injury and neointima formation increase MMP-9 expression and MMP-2 activation in human saphenous vein. Cardiovasc Res. 1997;33(2): 447-59.
Goldman, et al. Degradation of alpha-actin filaments in venous smooth muscle cells in response to mechanical stretch. Am J Physiol Heart Circ Physiol. 2003;284(5): H1839-47.
Goldman, et al. Negative regulation of vascular smooth muscle cell migration by blood shear stress. Am J Physiol Heart Circ Physiol. 2007;292(2): H928-38.
Greenwood, et al. Restructuring of focal adhesion plaques by pi 3-kinase. Regulation by ptdins (3,4,5)-p(3) binding to alpha-actinin. J Cell Biol. 2000;150(3): 627-42.
Grote, et al. Mechanical stretch enhances mRNA expression and proenzyme release of matrix metalloproteinase-2 (MMP-2) via nad(p)h oxidase-derived reactive oxygen species. Circulation Research. 2003;92(11): 80-6.
Guan, et al. Synthesis, characterization, and cytocompatibility of elastomeric, biodegradable poly(ester-urethane)ureas based on poly(caprolactone) and putrescine. J Biomed Mater Res. 2002;61(3): 493-503.
Gusic, et al. Shear stress and pressure modulate saphenous vein remodeling ex vivo. J Biomech. 2005;38(9): 1760-9.
Hayashi, K. Experimental approaches on measuring the mechanical properties and constitutive laws of arterial walls. J Biomech Eng. 1993;115(4B): 481-8.
He et al., Arterial Replacement with Compliant Hierarchic Hybrid Vascular Graft: Biomechanical Adaptation and Failure Tissue Engineering, 2002, pp. 213-224, 8(2).
Hermans, et al. Fibrin: structure and interactions. Seminars in thrombosis and hemostasis. vol. 8. No. 1. 1982.
Hilker, et al. Bypass graft disease: Analysis of proliferative activity in human aorto-coronary bypass grafts. Heart Surg Forum. 2002;5 Suppl 4: S331-41.
Hu, et al. Activation of pdgf receptor alpha in vascular smooth muscle cells by mechanical stress. Faseb J. 1998;12(12): 1135-42.
Huynh, et al. Alterations in wall tension and shear stress modulate tyrosine kinase signaling and wall remodeling in experimental vein grafts. J Vasc Surg. 1999;29(2): 334-44.
Huynh, et al. External support modulates g protein expression and receptor coupling in experimental vein grafts. Surgery. 1999;126(2): 127-34.
Igase, et al. Apoptosis and bcl-xs in the intimal thickening of balloon-injured carotid arteries. Clin Sci (Loud). Jun. 1999;96(6): 605-12.
International search report and written opinion dated Mar. 1, 2014 for EP Application No. 11810266.4.
International search report and written opinion dated Mar. 9, 2012 for PCT Application No. US2011/044510.
Izzat, et al. Influence of external stent size on early medial and neointimal thickening in a pig model of saphenous vein bypass grafting. Circulation 1996; 94:1741-5.
Jacot, et al. Early adaptation of human lower extremity vein grafts: Wall stiffness changes accompany geometric remodeling. J Vasc Surg. 2004;39(3): 547-55.
Jeremy, et al. A bioabsorbable (polyglactin), nonrestrictive, external sheath inhibits porcine saphenous vein graft thickening. J Thorac Cardiovasc Surg. 2004;127(6): 1766-72.
Jeremy, et al. Nitric oxide synthase and adenylyl and guanylyl cyclase activity in porcine interposition vein grafts. Ann Thorac Surg. 1997;63(2): 470-6.
Jiang, et al. A novel vein graft model: Adaptation to differential flow environments. Am J Physiol Heart Circ Physiol. 2004;286(1): H240-5.
Jiang, et al. Wall shear modulation of cytokines in early vein grafts. J Vasc Surg. 2004;40(2): 345-50.
Kamenz, et al. Incidence of intimal proliferation and apoptosis following balloon angioplasty in an atherosclerotic rabbit model. Cardiovasc Res. 2000;45(3): 766-76.

(56) References Cited

OTHER PUBLICATIONS

Kanjickal, et al. Polymeric sustained local drug delivery system for the prevention of vascular intimal hyperplasia. J Biomed Mater Res A. 2004;68(3): 489-95.
Karayannacos, et al. Late failure in vein grafts: Mediating factors in subendothelial fibromuscular hyperplasia. Ann Surg. 1978;187(2): 183-8.
Kohler, et al. Inhibition of neointimal hyperplasia in a sheep model of dialysis access failure with the bioabsorbable vascular wrap paclitaxel-eluting mesh. J Vasc Surg. 2007;45(5): 1029-1037; discussion 1037-8.
Kohler, et al. The effect of rigid external support on vein graft adaptation to the arterial circulation. J Vasc Surg. 1989;9(2): 277-85.
Labadie, et al. Pulsatile perfusion system for ex vivo investigation of biochemical pathways in intact vascular tissue. Am J Physiol Heart Circ Physiol. 1996;270(2): H760-8.
Lafleur, et al. Activation of pro-(matrix metalloproteinase-2) (pro-mmp-2) by thrombin is membrane-type-mmp-dependent in human umbilical vein endothelial cells and generates a distinct 63 kda active species. Biochem J. 2001;357(Pt 1): 107-15.
Lee, et al. Nanofiber alignment and direction of mechanical strain affect the ECM production of human ACL fibroblast. Biomaterials 2005;26(11):1261-1270.
Lee, et al. Theoretical hydraulic consequences of vein graft taper. Journal of Vascular Surgery. 2003, 38: 785-792.
Levorson, et al. Fabrication and characterization of multiscale electrospun scaffolds for cartilage regeneration. Biomed Mater 2013;8:014103. doi:10.1088/1748-6041/8/1/014103.
Liao, et al. A novel time-varying poly lactic-co glycolic acid external sheath for vein grafts designed under physiological loading. Tissue Eng. 2007;13(12): 2855-62.
Lignen, et al. Tissue inhibitor of matrix metalloproteinases-1 impairs arterial neointima formation after vascular injury in mice. Circ Res. 1999;85(12): 1186-91.
Ligush, et al. Evaluation of endothelium-derived nitric oxide mediated vasodilation utilizing ex vivo perfusion of an intact vessel. J Surg Res. 1992;52(5): 416-21.
Liu, et al. A possible role of initial cell death due to mechanical stretch in the regulation of subsequent cell proliferation in experimental vein grafts. Biomech Model Mechanobiol. 2002;1(1): 17-27.
Liu, et al. Changes in the organization of the smooth muscle cells in rat vein grafts. Ann Biomed Eng. 1998;26(1): 86-95.
Liu, et al. Partial prevention of monocyte and granulocyte activation in experimental vein grafts by using a biomechanical engineering approach. J Biomech. 1999;32(11): 1165-75.
Liu, et al. The signaling protein rho is necessary for vascular smooth muscle migration and survival but not for proliferation. Surgery. 2002;132(2): 317-25.
Mavromatis, et al. Early effects of arterial hemodynamic conditions on human saphenous veins perfused ex vivo. Arterioscler Thromb Vasc Biol. 2000;20(8): 1889-95.
McManus, et al. Electrospun fibrinogen: feasibility as a tissue engineering scaffold in a rat cell culture model. Journal of Biomedical Materials Research Part A 81.2 (2007): 299-309.
McManus, et al. Mechanical properties of electrospun fibrinogen structures. Acta Biomaterialia 2.1 (2006): 19-28.
Mehta, et al. External stenting reduces long-term medial and neointimal thickening and platelet derived growth factor expression in a pig model of arteriovenous bypass grafting. Nat Med. 1998;4(2): 235-9.
Meng, et al. Mechanical stretching of human saphenous vein grafts induces expression and activation of matrix-degrading enzymes associated with vascular tissue injury and repair. Exp Mol Pathol. 1999;66(3): 227-37.
Morinaga, et al. Effect of wall shear stress on intimal thickening of arterially transplanted autogenous veins in dogs. J Vasc Surg. 1985;2(3): 430-3.

Morisaki, et al. Cell cycle-dependent inhibition of DNA synthesis by prostaglandin i2 in cultured rabbit aortic smooth muscle cells. Atherosclerosis. 1988;71(2-3): 165-71.
Moritz et al., A Method for Constricting Large Veins for Use in Arterial Vascular Reconstruction, Artificial Organs, 1990, pp. 394-398, 14(5).
Morton, et al. Electrospun fibrin nanofibers for the use in tissue engineering. Modification of fibrin to improve applications in regenerative medicine (2010): 81.
Mosesson, M. W. Fibrinogen and fibrin structure and functions. Journal of Thrombosis and Haemostasis 3.8 (2005): 1894-1904.
Muluk, et al. Enhancement of tissue factor expression by vein segments exposed to coronary arterial hemodynamics. Journal of Vascular Surgery: Official Publication, the Society for Vascular Surgery Land] International Society for Cardiovascular Surgery, North American Chapter. 1998;27(3): 521-7.
Murphy-Ullrich, et al. Focal adhesion integrity is downregulated by the alternatively spliced domain of human tenascin. J Cell Biol. 1991;115(4): 1127-36.
Murphy-Ulrich, JE. The de-adhesive activity of matricellular proteins: Is intermediate cell adhesion an adaptive state? J Clin Invest. 2001;107(7): 785-90.
Nagai et al., Identification of Two Types of Smooth Muscle Myosin Heavy Chain Isoforms by eDNA Cloning and Immunoblot Analysis, The Journal of Biological Chemistry, Jun. 15, 1989, pp. 9734-9737, 264(17).
Nakazawa, et al. Smooth muscle cell migration induced by shear-loaded platelets and endothelial cells. Enhanced platelet-derived growth factor production by shear-loaded platelets. Int Angiol. 2000;19(2): 142-6.
Nedovic, et al. Cell immobilisation by electrostatic droplet generation. Landbauforsch Volk 2002, (241) 11-17.
Newby, et al. Extracellular matrix degrading metalloproteinases in the pathogenesis of arteriosclerosis. Basic Res Cardiol. 1994;89(Suppl 1): 59-70.
Nikolopoulos, et al. Integrin-linked kinase (ilk) binding to paxillin ldl motif regulates ilk localization to focal adhesions. J Biol Chem. 2001;276(26): 23499-505.
Nishibe, et al. Induction of angiotensin converting enzyme in neointima after intravascular stent placement. Int Angiol. 2002;21(3): 250-5.
Notice of allowance dated May 10, 2016 for U.S. Appl. No. 13/811,206.
Office action dated May 8, 2015 for U.S. Appl. No. 13/811,206.
Office action dated Nov. 18, 2015 for U.S. Appl. No. 13/811,206.
Parsonnet, et al. New stent for support of veins in arterial grafts. Arch Surg. 1963;87: 696702.
Perumchery, et al. A Novel Method for the Fabrication of Fibrin-Based Electrospun Nanofibrous Scaffold for Tissue-Engineering Applications*. Tissue Engineering Part C: Methods 17.11 (2011): 1121-1130.
Pintucci, et al. Anti-proliferative and anti-inflammatory effects of topical mapk inhibition in arterialized vein grafts. Faseb J. 2006;20(2): 398-400.
Porter, et al. Marimastat inhibits neointimal thickening in a model of human vein graft stenosis. Br J Surg. 1998;85(10): 1373-7.
Porter, et al. Production and inhibition of the gelatinolytic matrix metalloproteinases in a human model of vein graft stenosis. Eur J Vasc Endovasc Surg. 1999;17(5): 404-12.
Porter, et al. Simvastatin inhibits human saphenous vein neointima formation via inhibition of smooth muscle cell proliferation and migration. J. Vasc. Surg. 2002;36: 150-7.
Porter, et al. The development of an in vitro flow model of human saphenous vein graft intimal hyperplasia. Cardiovasc Res. 1996;31(4): 607-14.
Powell, et al. Matrix-specific effect of endothelial control of smooth muscle cell migration. J Vasc Surg. 1996;24(1): 51-7.
Predel, et al. Implications of pulsatile stretch on growth of saphenous vein and mammary artery smooth muscle. Lancet. 1992;340(8824): 878-9.
Qian, et al. Gene expression of bfgf and intimal hyperplasia of autologous vein grafts in rats. Zhonghua Yi Xue Za Zhi. 1996;76(11): 826-8.

(56) References Cited

OTHER PUBLICATIONS

Ramos, et al. Histologic fate and endothelial changes of distended and nondistended vein grafts. Ann Surg. 1976;183(3): 205-28.
Redmond, et al. Effect of pulse pressure on vascular smooth muscle cell migration: The role of urokinase and matrix metalloproteinase. Thrombosis & Haemostasis. 1999;81(2): 293-300.
Resnick, et al. Hemodynamic forces are complex regulators of endothelial gene expression. The Faseb J. 1995;9(10): 874-82.
Rho, et al. Electrospinning of collagen nanofibers: Effects on the behavior of normal human keratinocytes and early-stage wound healing. Biomaterials. 2006;27(8): 1452-61.
Sage, et al. Extracellular proteins that modulate cell-matrix interactions. Sparc, tenascin, and thrombospondin. J Biol Chem. 1991;266(23): 14831-4.
Sell, et al. Cross-linking methods of electrospun fibrinogen scaffolds for tissue engineering applications. Biomedical Materials 3.4 (2008): 045001.
Severyn, et al. The influence of hemodynamics and wall biomechanics on the thrombogenicity of vein segments perfused in vitro. J Surg Res. 2004;121(1): 31-7.
Shigematsu, et al. Direct and indirect effects of pulsatile shear stress on the smooth muscle cell. Int Angiol. 2000;19(1): 39-46.
Sho, et al. Subnormal shear stress-induced intimal thickening requires medial smooth muscle cell proliferation and migration. Exp Mol Pathol. 2002;72(2): 150-60.
Simosa, et al. Survivin expression is up-regulated in vascular injury and identifies a distinct cellular phenotype. J Vasc Surg. 2005;41(4): 682-90.
Soletti et al., A Bi-layered Elastomeric Scaffold for Tissue Engineering of Small-Diameter Vascular Grafts, Acta Biomater., Jan. 2010, pp. 110-122, 6(1).
Sreerekha, et al. Fabrication of fibrin based electrospun multiscale composite scaffold for tissue engineering applications. Journal of biomedical nanotechnology 9.5 (2013): 790-800.
Stankus, et al. Fabrication of biodegradable elastomeric scaffolds with sub-micron morphologies. J Biomed Mater Res A. 2004;70(4): 603-14.
Stankus, et al. Fabrication of cell microintegrated blood vessel constructs through electrohydrodynamic atomization. Biomaterials. 2007;28:2738-46.
Stankus, et al. Microintegrating smooth muscle cells into a biodegradable, elastomeric fiber matrix. Biomaterials. 2006;27(5): 735-44.
Stitzel, et al. Controlled fabrication of a biological vascular substitute. Biomaterials. 2006, 27: 1088-1094.
Stooker, et al. Perivenous application of fibrin glue reduces early injury to the human saphenous vein graft wall in an ex vivo model. European Journal of Cardio-thoracic Surgery. 2002, 21: 212-217.
Stooker, et al. Pressure-diameter relationship in the human greater saphenous vein. Ann Thorac Surg. 2003;76(5): 1533-8.
Szilagyi, et al. Biologic fate of autogenous vein implants as arterial substitutes: Clinical, angiographic and histopathologic observations in femoro-popliteal operations for atherosclerosis. Ann Surg. 1973;178(3): 232-46.
Tai, et al. Compliance properties of conduits used in vascular reconstruction. Br J Surg. 2000;87(11): 1516-24.
Traver, et al. New Generation Tissue Sealants and Hemostatic Agents: Innovative Urologic Applications. Reviews in Urology. 2006, 8: 104-111.
Tu, et al. Migfilin and mig-2 link focal adhesions to filamin and the actin cytoskeleton and function in cell shape modulation. Cell. 2003;113: 37-47.
Tyagi, et al. Stretch-induced membrane type matrix metalloproteinase and tissue plasminogen activator in cardiac fibroblast cells. J Cell Physiol. 1998;176(2): 374-82.
Uzui, et al. The role of protein-tyrosine phosphorylation and gelatinase production in the migration and proliferation of smooth muscle cells. Atherosclerosis. 2000;149(1): 51-9.
Veazey, et al. Mammalian cell delivery via aerosol deposition. J. Biomed. Mater. Res. 2005 (72B)334-8.
Vijayan, et al. Long-term reduction of medial and intimal thickening in porcine saphenous vein grafts with a polyglactin biodegradable external sheath. J Vasc Surg. 2004;40(5): 1011-9.
Vorp, et al. A device for the application of cyclic twist and extension on perfused vascular segments. Am J Physiol Heart Circ Physiol. 1996;270(2): H787-95.
Vorp, et al. Modeling the transmural stress distribution during healing of bioresorbable vascular prostheses. Ann Biomed Eng. 1995;23(2): 178-88.
Wan, et al. Differential, time-dependent effects of perivenous application of fibrin glue on medial thickening in porcine saphenous vein grafts. European Journal of Cardio-thoracic Surgery, 29, (2006): 742-747.
Wang, et al. Expression of apoptosis-related proteins and structural features of cell death in explanted aortocoronary saphenous vein bypass grafts. Cardiovasc Surg. 2001;9(4): 31928.
Wang, et al. Regulation of vein graft hyperplasia by survivin, an inhibitor of apoptosis protein. Arterioscler Thromb Vasc Biol. 2005;25(10): 2081-7.
Weisel, et al. Computer modeling of fibrin polymerization kinetics correlated with electron microscope and turbidity observations: clot structure and assembly are kinetically controlled. Biophysical journal 63.1 (1992): 111.
Weisel, et al. Mechanisms of fibrin polymerization and clinical implications. Blood 121.10 (2013): 1712-1719.
Wesly, et al. Static linear and nonlinear elastic properties of normal and arterialized venous tissue in dog and man. Circulation Research (Online). 1975;37(4): 509-20.
Wnek, et al. Electrospinning of nanofiber fibrinogen structures. Nano Letters 3.2 (2003): 213-216.
Wolf, et al. Antibodies against transforming growth factor-beta 1 suppress intimal hyperplasia in a rat model. J Clin Invest. 1994;93(3): 1172-8.
Wolff, et al. Transforming growth factor-beta1 antisense treatment of rat vein grafts reduces the accumulation of collagen and increases the accumulation of h-caldesmon. J Vasc Surg. 2006;43(5): 1028-36.
Wu, C. Integrin-linked kinase and pinch: Partners in regulation of cell-extracellular matrix interaction and signal transduction. J Cell Sci. 1999;112 (Pt 24): 4485-9.
Wu, et al. Integrin-linked kinase (ILK) and its interactors: A new paradigm for the coupling of extracellular matrix to actin cytoskeleton and signaling complexes. J Cell Biol. 2001;155(4): 505-10.
Xu, et al. Aligned biodegradable nanofibrous structure: a potential for blood vessel engineering. Biomaterials Feb. 2004; 25(5): 877-86.
Xu, et al. Electrospun Nanofiber Fabrication as Synthetic Extracellular Matrix and Its Potential for Vascular Tissue Engineering. Tissue Engineering, vol. 10, No. 7/8, 2004.
Yamaoka, et al. Timp-1 production by human scleral fibroblast decreases in response to cyclic mechanical stretching. Opthalmic Research. 2001;33(2): 98-101.
Yu, et al. Electrospinning, Encyclopedia of Polymer Science & Technology (2008) 1-20.
Zhang, et al. Association of smooth muscle cell phenotypic modulation with extracellular matrix alterations during neointima formation in rabbit vein grafts. J Vasc Surg. 1999;30(1): 169-83.
Zilla, et al. Constrictive external nitinol meshes inhibit vein graft intimal hyperplasia in nonhuman primates. The Journal of Thoracic and Cardiovascular Surgery 2008;136:717-725.
Zilla, et al. Utilization of shape memory in external vein-graft meshes allows extreme diameter constriction for suppressing intimal hyperplasia: A non-human primate study. J Vasc Surg 2009;49:1532-42.
Zuckerbraun, et al. Overexpression of mutated ikappabalpha inhibits vascular smooth muscle cell proliferation and intimal hyperplasia formation. J Vasc Surg. 2003;38(4): 812-9.
Zwolak, et al. Kinetics of vein graft hyperplasia: Association with tangential stress. Journal of Vascular Surgery: Official Publication, the Society for Vascular Surgery [and] International Society for Cardiovascular Surgery, North American Chapter. 1987;5(1): 12636.

\* cited by examiner

GRAFT DEVICES AND METHODS OF USE

CROSS-REFERENCE TO RELATED APPLICATION

This application is a continuation of U.S. patent application Ser. No. 13/811,206 filed Aug. 14, 2013, now issued as U.S. Pat. No. 9,445,874, which is a National Phase of International Application No. PCT/US2011/044510 filed Jul. 19, 2011, which claims the benefit of priority to U.S. Provisional Application No. 61/365,612 filed Jul. 19, 2010, each of which is incorporated herein by reference in its entirety.

DESCRIPTION OF THE INVENTION

Field of the Invention

The present invention relates generally to graft devices for a mammalian patient. In particular, the present invention provides a cartridge device for insertion into an electrospinning unit.

BACKGROUND OF THE INVENTION

Coronary artery disease, leading to myocardial infarction and ischemia, is currently the number one cause of morbidity and mortality worldwide. Current treatment alternatives consist of percutaneous transluminal angioplasty, stenting, and coronary artery bypass grafting (CABG). CABG can be carried out using either arterial or venous conduits and is an effective and widely used treatment to combat coronary arterial stenosis, with nearly 500,000 procedures being performed annually. In addition, there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter, and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed arterial vein grafts (AVGs) will typically die or require re-operation.

IH accounts for 20% to 40% of all AVG failures within the first 5 years. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH can be initiated by the abrupt exposure of the veins to the dynamic mechanical environment of the arterial circulation.

For these and other reasons, there is a need for devices and methods which provide enhanced AVGs and other grafts for mammalian patients. Desirably the devices will improve long term patency and minimize surgical and device complications.

SUMMARY

Developing a reliable means to prevent the early events of the IH process would contribute to improvements in the outcome of arterial bypass procedures. Therefore, provided herein is a method of mechanically conditioning and otherwise treating and/or modifying an arterial vein graft, or any tubular tissue (living cellular structure) or artificial graft, typically, but not exclusively, in autologous, allogeneic xenogeneic transplantation procedures. To this end, provided herein is a method of wrapping a tubular graft, including, without limitation: vein; artery; lymphatic duct; vas deferens; tear duct; intestine; esophagus; ureter; urethra; trachea; bronchi; duct tissue; Eustachian tube; fallopian tube; and combinations of these (meaning the entire structure or a portion of those tissues). The graft is placed in a cartridge device and wrapped with a fiber matrix, typically with a biodegradable (also referred to as bioerodible or bioresorbable) polymer around the outer surface of the tubular tissue. In some embodiments, the matrix is deposited onto tubular tissue by electrospinning. In some embodiments, the tubular tissue is a vein, such as a saphenous vein, that is used, for instance, in an arterial bypass procedure, such as a coronary artery bypass procedure.

This new approach would have two potential applications. In the first non-limiting application, the matrix can be used as a peri-surgical tool for the modification of vein segments intended for use as an AVG. The modification of the vein or other tubular structure would be performed by treating the structure at bedside, immediately after removal from the body and just prior to grafting. In one non-limiting example, after the saphenous vein is harvested, and while the surgeon is exposing the surgical site, the polymer wrap would be electrospun onto the vein just prior to it being used for the bypass procedure.

According to a first aspect of the invention, a cartridge device for applying a fiber matrix to a tubular member is disclosed. The cartridge device typically comprises a housing, a tubular member holder, a rotational element, and a polymer delivery assembly. A tubular member, such as a saphenous vein graft, can be placed over the tubular member holder, typically a mandrel, and the assembly is inserted into a chamber of the housing. The rotational element is located at one or more ends of the mandrel or a coupling or other element attached thereto, and is configured to attach to a rotational drive assembly, such as a rotational drive of an electrospinning unit. Electrical power or signals can be transmitted from outside of the housing to the mandrel, such as via a rotating connector of the rotational element. A polymer delivery assembly is integral to the housing or attachable thereto, and can contain one or more polymers, solvents, agents or other material to be applied in fiber form to the outside of the tubular member.

In some embodiments, the housing is conductive or includes a conductive coating, and a Farraday cage effect is created to minimize adverse effects of the electric field used in an electrospinning process. The housing can be grounded or maintained at a positive or negative charge.

In some embodiments, the polymer delivery assembly includes a single or multi-compartment reservoir comprising flowable materials or materials that can be made flowable during the electrospinning process. The polymer delivery assembly can include one or more mixing elements configured to mix material from the one or more compartments. A pump assembly can be included, such as a syringe pump, to cause the polymer and other components to enter a nozzle, where the nozzle can be integral to the cartridge or a separate component.

In some embodiments, the cartridge includes an integral nozzle, such as a fixed nozzle, or a nozzle configured to move in a linear and/or non-linear path. One or more drive mechanisms can be included to cause translational and/or rotational movement of the nozzle. Multiple nozzles can be included in the cartridge, such as to deliver similar or dissimilar polymer mixtures, simultaneously or sequentially.

In some embodiments, the cartridge includes one or more tubes, such as saphenous vein graft segments or artificial tubes with impedances approximating saphenous vein graft segments, which are placed over the ends of the mandrel proximate the ends of the tubular member to which the fiber matrix is to be applied.

In some embodiments, the cartridge includes one or more sensors, such as sensors configured to measure one or more process parameters of applying a fiber matrix to the tubular member. Sensed parameters include but are not limited to: fiber diameter; solvent parameter such as an airborne solvent parameter or solvent partial pressure parameter; force such as force used to control the tubular member holder tension; fiber matrix thickness; fiber matrix diameter; polymer parameter; velocity parameter such as mandrel rotational velocity or fiber velocity; electric field parameter; and combinations thereof.

According to another aspect of the invention, a system for applying a fiber matrix to a tubular member is disclosed. The system can comprise a cartridge device of the present invention and an electrospinning unit. The system is preferably operated at one or more parameters listed in Table 1 herebelow. The system can include multiple cartridges, such as to apply a fiber matrix to multiple vein grafts, or a single cartridge can be used to process one or more vein grafts. The electrospinning unit can be configured to process a single cartridge at a time, or multiple cartridges simultaneously. Typically, the process time for a single cartridge ranges from 10 minutes to 20 minutes. The system can include sensors to determine the integrity of one or more connections, such as electrical and/or fluid connections between or within the cartridge device and the electrospinning unit. The system can include one or more measurement devices, such as a laser micrometer or a camera system configured to measure one or more system parameters, such as component location or dimensional information that can be used by the system to adjust one or more system parameters in real time, or activate a warning or alarm system.

According to yet another aspect of the invention, a method of applying a fiber matrix to a tubular member is disclosed. A cartridge device is selected comprising a housing, a tubular member holder, a rotational element and a polymer delivery assembly. A tubular member, such as a saphenous vein graft, is inserted over the tubular member holder, and the assembly is inserted into the housing of the cartridge. A fiber matrix is applied to the tubular member, such as with an electrospinning unit in which the cartridge has been inserted. The tubular member can comprise tissue which has been formed or reformed into a tubular structure, such as a flat sheet which has been formed into a tube. One or more tubes, such as segments of saphenous vein or artificial tubes whose impedance approximates saphenous vein impedance can be inserted onto the ends of the tubular member holder prior to insertion into the cartridge. The tubes can be configured to maintain position of the tubular member and/or to create a uniform electric field during the electrospinning process along the length of the tubular member holder. The procedure is performed in a manner to maintain sterility of at least the tubular member, such as for implantation into a living patient.

BRIEF DESCRIPTION OF THE DRAWINGS

The accompanying drawings, which are incorporated in and constitute a part of this specification, illustrate various embodiments of the present invention, and together with the description, serve to explain the principles of the invention. In the drawings.

DETAILED DESCRIPTION OF THE DRAWINGS

Figure 1:
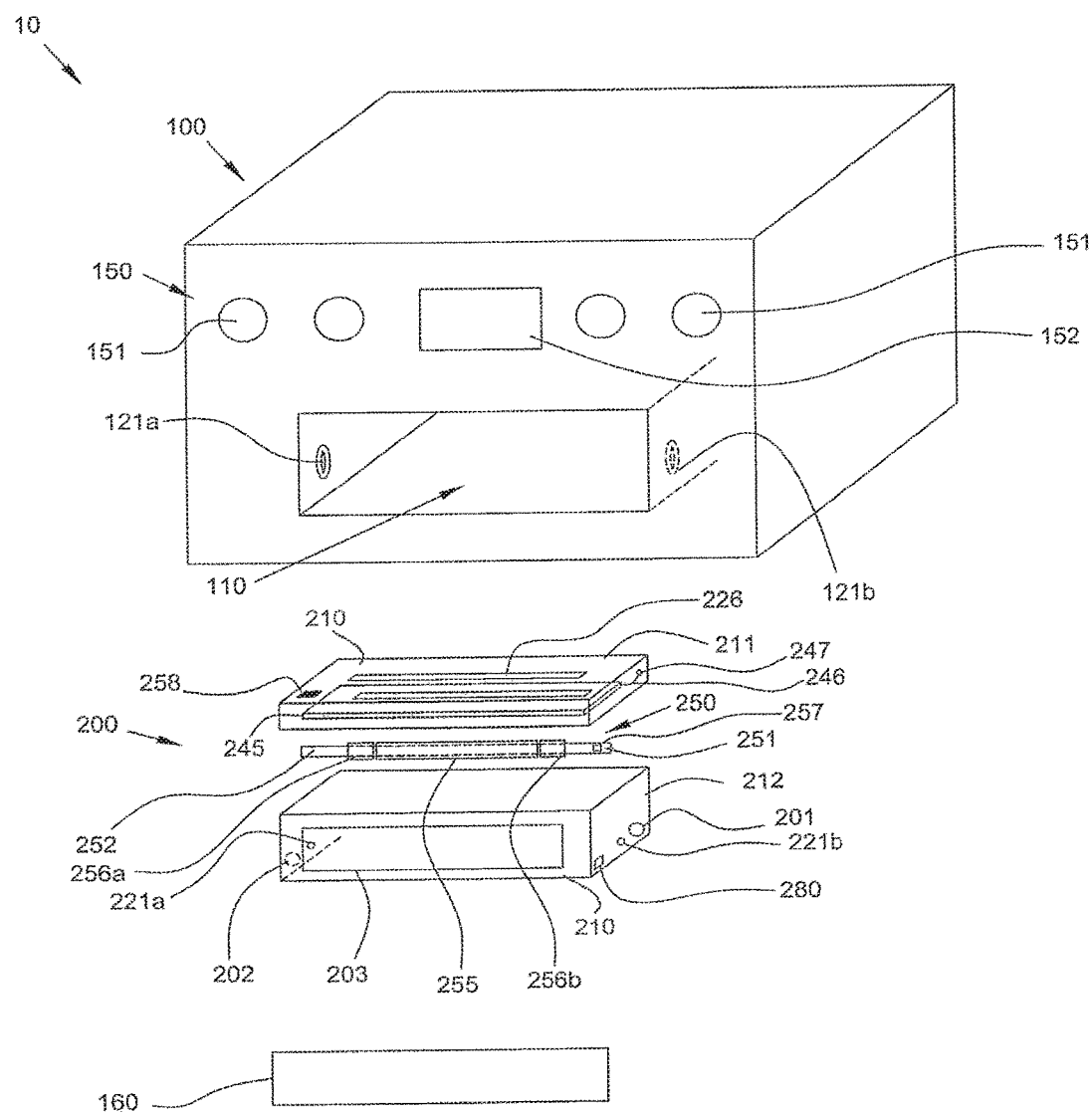
FIG. 1 illustrates a perspective view of a system for applying a fiber matrix to a tubular member, consistent with the current invention.

Reference will now be made in detail to the present embodiments of the invention, examples of which are illustrated in the accompanying drawings. Wherever possible, the same reference numbers will be used throughout the drawings to refer to the same or like parts.

Provided herein is a cartridge device for insertion into a fiber application unit, such as an electrospinning unit or other piece of equipment constructed and arranged to apply a fiber such as a polymer fiber around or at least a portion of the outer surface of a tubular member, such as a harvested blood vessel. The cartridge device comprises a housing that defines a chamber. A tubular member holder, such as a mandrel, is inserted into the chamber, and the cartridge device is inserted into the fiber application unit. The fiber application unit drives rotation element of the cartridge device to rotate the mandrel while one or more types of fibers, such as polymer fibers, are applied through polymer delivery assembly integral to the cartridge device. The cartridge device can be sterile or can provide a sterile and/or aseptic chamber. The cartridge is typically used in a sterile procedure, such as to maintain a processed tubular member in a sterile state for implantation in a patient. The cartridge device can include one or more elements for transferring to the cartridge device or to a location inside the cartridge device, one or more of: a force such as rotational force, electrical power or signals, or specific environmental conditions such as specific temperature or humidity conditions. The cartridge can include one or more drive assemblies, such as linear or rotational drive assemblies. In some embodiments, an integral nozzle is mounted on a drive assembly.

The graft device produced by the devices and systems described herein includes a tubular member and covering, and is typically a hollow tube tubular member used as a connection for fluid to flow between a first body space and a second body space. The tubular member can comprise tissue, such as autologous, allogeneic, or xenogeneic tissue, including, without limitation: vein; artery; lymphatic duct; vas deferens; tear duct; intestine; esophagus; ureter; urethra; trachea; bronchi; duct tissue; Eustachian tube; fallopian tube; and combinations of these (meaning the entire structure or a portion of those tissues). The tubular member can also be a tissue engineered vascular graft, comprised of a covering material (biological or synthetic-based) that is seeded with adult differentiated cells and/or undifferentiated stem cells, or unseeded. The covering can be treated with synthetic, biological, or biomimetic cues to enhance anti-thrombogenicity or selective or non-selective cell repopulation once implanted in vivo. The covering can be treated with one or more chemotactic or chemoattractant agents and can include selective degradation sites. Alternatively or additionally, the tubular member can include an artificial, non-tissue, structure, such as polytetrafluoroethylene (PTFE); expanded PTFE (ePTFE); polyester; polyvinylidene fluoride/hexafluoropropylene (PVDF-HFP); silicone; polyethylene; polypropylene; polyester based polymer; polyether based polymer; thermoplastic rubber; and combinations of these. The tubular member can have a relatively uniform cross section, or a cross section that varies (e.g. in diameter or cross sectional geometry) along the length of the tubular member. The tubular member can be straight or curved. Additional graft devices, systems and methods are also described in applicant's co-pending U.S. Provisional Patent Application Ser. No. 61/286,820, filed Dec. 16, 2009, entitled "Graft Devices and Methods for Use," and applicant's co-pending U.S. Provisional Patent Application Ser. No. 61/291,820, filed Dec. 31, 2009, entitled "Graft Devices and Methods of Fabrication", each of which are incorporated by reference herein in its entirety.

The applied fiber is typically a polymer or polymer blend fiber that is applied when the one or more polymers are mixed with one or more solvents. Alternatively or additionally, polymers can be applied in liquid form achieved through other means such as by elevated temperature or by the use of prepolymerized monomers which are activated and polymerized during or shortly after processing. Typical polymers include natural polymers, synthetic polymers, and blends of natural and synthetic polymers. For example and without limitation, natural polymers include silk, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers.

As used herein, the descriptors "flow conduit" and "tubular member" do not refer specifically to a geometrically perfect tube having a constant diameter and a circular cross-section. It also embraces tissue and artificial conduits having non-circular and varying cross sections, and can have a variable diameter, and thus any shape having a contiguous wall surrounding a lumen (that is, they are hollow), and two openings into the lumen such that a liquid, solid or gas can travel from one opening to the other. The flow conduit can be created from a membranous material, such as a membrane that comprises a sheet that is joined along a seam to create a substantially cylindrical form. The flow conduit can comprise harvested tissue that is formed or reformed into a tube or other structure.

The covering typically is substantially or essentially contiguous about an internal or external wall of a flow conduit or other tubular member, meaning that the covering forms a continuous, supportive ring on a surface and about a circumference of a portion, but not necessarily over the entire surface (e.g., length) of the tubular member. The covering can be "restrictive", meaning that the covering is in substantial contact with the outer surface of the tubular member such as to provide an incremental physical property in addition to the underlying property of the tubular member. Alternatively, the covering can be narrowly spaced and proximate to the outer surface of the tubular member (e.g. to restrict after an initial unrestricted expansion). The covering can also be "constrictive", meaning that the diameter of the tubular member is reduced by the application of the covering. Restrictive coverings can be used to reinforce, restrict, hinder and/or limit (e.g., prevent) substantial circumferential expansion of the tubular member, such as when the graft device is a flow conduit used as a bypass graft and is exposed to arterial pressure; or otherwise when the tubular member is radially expanded. The degree of restriction by the covering typically is such that when exposed to internal pressure, such as typical arterial pressures, the tubular member is prevented from distending to the extent that would occur without such restriction. Constrictive coverings can be used to match the internal diameter of the tubular member to the internal diameter of the target tissue being connected by the tubular member. For example, quite often a vein being used as a coronary artery bypass graft has a considerably larger internal diameter than the target coronary artery being bypassed. In order to reduce flow disturbances, it is advantageous to match the internal diameter of the graft (tubular member) to the internal diameter of the bypassed coronary artery. The covering can be durable or temporary, such as when the restrictive nature of a biodegradable covering can decline over time. The covering can have a relatively uniform cross section, or a cross section that varies along the length of the covering.

The covering can be applied to a tubular member that has either a cylindrical or non-cylindrical mandrel inserted in its lumen. Mandrels are typically constructed and arranged to be removed from the graft device described herein without damaging the tubular member or any other portion of the graft device. The mandrel can comprise an expandable tube, such as a furled tube or other radially or axially expandable structure, such that the mandrel can be unfurled or otherwise radially or axially constricted for atraumatic removal from the tubular member of the graft device. The mandrel can transform from a rigid state to a flexible state, and vice versa.

The mandrel can be relatively straight, or can have a non-linear geometry, such as a three dimensional geometry intended to match anatomical locations of a patient, such as an anatomical topography proximate two or more intended anastomotic connections for the graft device. The mandrel can be a malleable or otherwise deformable structure which is shaped during a surgical procedure. Alternatively, the mandrel can be fabricated based upon one or more patient images created during an imaging procedure, such as an imaging procedure selected from the group consisting of: X-ray such as still image X-ray or fluoroscopy; MRI, CT scan, NMR, ultrasound, PCT scan, CCD camera; film camera; and combinations of these.

In coverings applied to a tubular member with an electrospinning process, an electrically conductive mandrel, for example a rod that is formed of a conductive material such as stainless steel, can be placed inside a tubular conduit, such as a vein, and polymer fibers deposited about the circumference of at least a portion of the tissue by rotation or other movement of the mandrel, movement of the nozzles supplying the fiber, and/or movement of the electrical field directing the fibers toward the mandrel. Thickness of the covering can be controlled by adjusting the chemical or physical properties of the polymer solution to be deposited, increasing the infusion rate of the polymer solution, modifying the electric field between the polymer source and the mandrel or target, and/or adjusting duration of the electrospinning. Use of a more viscous polymer composition can result in thicker fibers, requiring less time to deposit a covering of a desired thickness. Use of a less viscous polymer composition can result in thinner fibers, requiring increased deposition time to deposit a covering of a desired thickness. The thickness of the covering and fibers within the covering affects both mechanical properties such as stiffness and buckling stability as well as the speed of biodegradation of the covering. Biodegradation can also be varied by altering the surface finish, wettability, porosity or other characteristic of the fibers. These parameters can be altered by using solvents or diluents that evaporate at varying rates and/or by adding purifiers to the solution, such as immiscible fluids, emulsified particles or undissolved solids that can be later dissolved such as to create pores. Alternatively or additionally, other modifying agents can be added to the polymer prior to electrospinning such as detergents or surfactants. These polymer solution parameters are optimized, depending on the end-use of the covering, to achieve a desired or optimal physiological effect. Thickness can be varied along the length of a target in a regular or irregular fashion, such as in creating a target that is thicker at one or both ends, in the center or as with a location-dependent symmetrical or asymmetrical thickness. In another particular embodiment, the thickness is varied by moving an electrospinning nozzle back and forth slowly near a specific circumferential location, thereby depositing more material proximate to that area. In yet another particular embodiment, covering thickness is determined by the thickness of the tubular member, such as when the covering is thicker at a circumferential portion of the tubular member that is thinner than other circumferential portions of the tubular member. In still yet another particular embodiment, thickness is varied by applying a field modification proximate to the polymer source or target to alter the trajectory of the fibers. Such a field modification could be produced, for example by a metal plate that is inserted into the area adjacent to the source or target that is at a sufficiently different voltage potential than the source such that the resulting field alters the trajectory of the fibers.

Electrospinning can be performed using two or more nozzles, wherein each nozzle can be a source of a different polymer solution. The nozzles can be biased with different biases or the same bias in order to tailor the physical and chemical properties of the resulting non-woven polymeric mesh. Additionally, multiple different targets (e.g. mandrels) can be used. When the electrospinning is to be performed using a polymer suspension, the concentration of the polymeric component in the suspension can also be varied to modify the physical properties of the matrix. For example, when the polymeric component is present at a relatively low concentration, the resulting fibers of the electrospun non-woven mesh have a smaller diameter than when the polymeric component is present at relatively high concentration. Without any intention to be limited by this theory, it is believed that lower polymer concentration solutions have a lower viscosity, leading to greater extrusion or attenuation of the fibers to produce thinner fibers. One skilled in the art can adjust polymer solution chemical and physical properties and process parameters to obtain fibers of desired characteristics, including fibers whose characteristics change along the length or width of the target.

Coverings can be constructed and arranged in a manner specific to a patient morphological or functional parameter. These parameters can be selected from the group consisting of: vessel size such as inside diameter, outside diameter, length, and/or wall thickness; taper or other geometric property of a harvested vessel or vessel intended for anastomotic attachment; size and location of one or more side branch ostium or antrum within the harvested vessel; patient age or sex; vessel elasticity or compliance; vessel vasculitis; vessel impedance; specific genetic factor or trait; and combinations of these.

Coverings of arterial vein grafts can be processed in a way to achieve a certain blood flow rate or shear stress within the treated arterial vein graft. In a typical configuration, shear stress within the arterial vein graft is between 2-30 dynes/$cm^2$, preferably 12-20 dynes/$cm^2$ is achieved. Coverings can be processed in a way to control the oxygen, nutrients, or cellular permeabilities between the extravascular tissues and the abluminal surface of the treated hollow tissue. Such permeabilities depend on the covering chemical and physical properties, the pore size distribution, porosity, and pore interconnectivity. Generally, oxygen, nutrients, and cellular (e.g., angiogenesis related cells, pericytes, endothelial cells, endothelial progenitor cells, inflammation-related cells; macrophages, etc.) permeability are required to improve the treated hollow tissue in vivo remodeling and healing process. To this end, the pore size ranges typically between 1 micron and 1000 microns, preferably between 100 microns and 250 microns, and the porosity ranges typically between 50% and 95%, preferably between 60% and 90%. The pores preferably are highly interconnected so that a relatively straight path along the radial direction of the fiber matrix can be traced from most of the pores across the total thickness of the matrix. Polymers used are typically hydrophilic.

Radial restriction and constriction of saphenous vein grafts has been achieved with stent devices placed over the vein prior to anastomosing the graft to the targeted vessels. The devices described herein can provide numerous advantages over the stent approaches. The devices described herein can have one or more parameters easily customized to a parameter of the harvested vessel and/or another patient parameter. The covering can be customized to a harvested vessel parameter such as geometry, such as to reduce the vein internal diameter to produce desired flow characteristics. The covering can be customized to a target vessel parameter (e.g., the aorta and diseased artery), such as to be compatible with vessel sizes, mechanical properties, and/or locations. The covering can be modified to simplify or otherwise improve the anastomotic connections, such as to be reinforced in the portion of the device that is anastomosed (e.g., portion where suture and/or clips pass through) and/or to protrude beyond the length of the tubular member and overlap other members connected to the graft device.

The devices described herein can be made to a wide array of lengths during the procedure, without the need for cutting, converse to the cutting of a stent device, which might create dangerously sharp edges. The covering is applied to the tubular member in a controlled, repeatable manner by an apparatus, such as an electro spinning instrument. The ends of the covering are atraumatic, limiting tissue damage or irritation at the anastomotic sites. In addition, the coverings described herein can be constructed and arranged to be easily and atraumatically removable, such as to apply another covering. Stent devices that are applied manually by a clinician require significant manipulation which could cause iatrogenic damage, have issues with reproducibility and accuracy limitations, and are difficult to reposition or remove, particularly without damaging the harvested vessel. The conformal covering follows the natural external geometry of the vessel (e.g., adventitial tissue accumulations, ligated branches, etc.) without resulting in a net inward compression caused by external application of a constant tubular structure onto a naturally variable tubular tissue.

As used herein, the term "polymer composition" is a composition comprising one or more polymers. As a class, "polymers" includes homopolymers, heteropolymers, co-polymers, block polymers, block co-polymers, alloys or blends and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic, non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, fibrin, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

The polymer or polymers typically will be selected so that it degrades in situ over a time period to optimize mechanical conditioning of the tissue. Non-limiting examples of useful in situ degradation rates include between 2 weeks and 1 year, and increments of 1, 2, 4, 8, 12, and, 24 weeks therebetween. Biodegradation can occur at different rates along different circumferential and/or axial portions of the covering. A biodegradation rate of the polymer covering can be manipulated, optimized or otherwise adjusted so that the covering degrades over a useful time period. For instance, in the case of a coronary artery bypass, it is desirable that the covering dissolves over 12 hours or, more typically, two weeks or more, so as to limit or prevent substantial sudden circumferential wall stress on the graft. The polymer degrades over a desired period of time so that the mechanical support offered by the polymer covering is gradually reduced over that period and the vein would be exposed to gradually increasing levels of circumferential wall stress (CWS).

The biodegradable polymers useful herein also can be elastomeric. Generally, any elastomeric polymer that has properties similar to that of the soft tissue to be replaced or repaired is appropriate. For example, in certain embodiments, the polymers used to make the wrap are highly distensible. Non-limiting examples of suitable polymers include those that have a breaking strain of from 100% to 1700%, more preferably between 200% and 800%, and even more preferably between 200% and 400%. Further, it is often useful to select polymers with tensile strengths between 10 kPa and 30 MPa, more preferably between 5 MPa and 25 MPa, and even more preferably between 8 MPa and 20 MPa. In certain embodiments, the elastic modulus calculated for physiologic levels of strain is between 10 kPa to 100 MPa, more preferably between 500 kPa and 10 MPa, and even more preferably between 0.8 MPa and 5 MPa.

In some embodiments, the graft devices described herein perform or is produced by one or more parameters listed in Table 1 immediately herebelow, typically with an electrospinning or other material application process:

TABLE 1

| Category | Typical and Preferred Settings |
|---|---|
| Covering Material: Applicable Polymers | Typical: PEUU (2-30%); PCL (5-35%); PCL:PGA/PLLA (5-35% - from 80:20 to 50:50); PCL:PLLA (5-35% - from 80:20 to 50:50); PVDF; PVDF-HFP; Silk-Fibroin<br>Preferred: PEUU (5-10%); PCL (5-15%); PCL:PGA (5-15% - 50:50); PCL:PLLA (5-15% - 50:50); PVDF; PVDF-HFP; Silk-Fibroin |

TABLE 1-continued

| Category | Typical and Preferred Settings |
|---|---|
| Covering Process Solvents (e.g., electrospin solvents, solvents for dipping or brush application) | Typical:<br>HFIP; DMSO; Chloroform; THF; DMF; Dichloromethane; DMAC, Dioxane; Toluene; Water; Acetone; Methanol; Propanol; Ethanol; Lithium Bromide; Aqueous Solutions (alkaline/acidic)<br>Preferred:<br>HFIP; DMF; THF; DMSO; Water<br>More Preferred<br>HFIP; Water |
| Covering Thickness | Typical:<br>50-1000 μm<br>Preferred:<br>50-200 μm<br>More Preferred:<br>50-150 μm |
| Covering $O_2$ Permeability | Typical<br>$10^{-10}$ to $10^{-6}$ ($cm^2$ mL $O_2$)/(s mL mmHg) |
| Covering Porosity | Typical<br>50%-95%<br>Preferred<br>85%-90% |
| Covering Average Pore Size | Typical<br>0.001-2.0 mm<br>Preferred<br>0.10-1.0 mm<br>Also Preferred<br>0.005-0.020 mm |
| Covering Compliance (measured in arterial-like conditions 70-110 mmHg) | Typical<br>$2\text{-}100 \times 10^{-4}$ $mmHg^{-1}$<br>Preferred (arterial blood applications)<br>$2\text{-}15 \times 10^{-4}$ $mmHg^{-1}$ |
| Covering Anastomotic Retention Force (e.g., suture retention) | Typical<br>1-10 N |
| Covering Circumferential Elastic Modulus (Static Elastic Modulus E) | Typical<br>0.5-2.0 MPa<br>Preferred<br>0.8-2.0 MPa |
| Covering Viscoelasticity (Dynamic Elastic Modulus G) | Typical<br>between 1-fold and 2-fold E |
| Covering Degradation Kinetics (in vivo complete resorption) | Typical<br>greater than 2 weeks<br>Preferred<br>linear reduction over 3-6 months |
| Covering Hardness | Typical<br>polymer Brinnell Scale between 5 and 40 |
| Covering Roughness | Typical<br>2-50 μM |
| Processing Time | Typical<br>10-20 minutes per vein graft (or other tubular member) |

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, a "fiber" comprises an elongated, slender, thread-like and/or filamentous structure. Fibers can be solid or hollow, and can have a smooth or porous surface.

As used herein, a "matrix" is any two- or three-dimensional arrangement of elements (e.g., fibers), either ordered (e.g., in a woven or non-woven mesh) or randomly-arranged (as is typical with a mat of fibers typically produced by electrospinning).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

Referring now to FIG. 1, a perspective view of an example system of the present invention is illustrated. System 10 comprises electrospinning unit 100 and cartridge 200. Electrospinning unit 100 comprises slot 110 that is sized and positioned to accept cartridge 200. Electrospinning unit 100 further comprises drive elements 121a and 121b that include one or more rotational drive assemblies configured to rotate in synchrony. Drive elements 121a and 121b can be synchronized with the use of a timing pulley. Alternatively or additionally, drive elements 121a and 121b can comprise two motors synchronized and/or otherwise controlled with optical encoders. Alternatively, a single drive element 121a can be incorporated, configured to drive a tubular member holder of cartridge 200 from one end, such as at drive end 252 of mandrel 250. Drive elements 121a and 121b can include numerous drive assembly components including but not limited to: a bearing such as a magnetically levitated bearing, a ball bearing, an air bearing or a pin bearing; a bushing; a torsion spring such as a torsion spring which is oscillated at its resonant frequency; a motor such as a DC motor, AC motor, synchronous motor or stepper motor, and combinations of these.

Cartridge 200 comprises mandrel 250 and a surrounding housing 210, comprising upper housing 211 and lower housing 212. Cartridge 200 can be slidingly received by slot 110 of electrospinning unit 100. Mandrel 250 may or may not be geometrically centered in the surrounding housing 210. Cartridge 200 can further comprise an internal chamber and an exterior surface between which a sterility barrier can exist. Alternatively, the entire cartridge 200 can be maintained sterile through its use. The housing 210, such as a portion or the entire exterior surface of the housing 210, can comprise an equipotential conductive surface such as an entire conductive surface defining a Faraday cage. The equipotential surface can be achieved with various elements including conductive paints or coatings or a conductive substance included in the housing material. The exterior surface can carry a positive, negative, or zero-potential (ground) charge.

Cartridge 200 comprises bar code 258 that is read by electrospinning unit 100 and provides an identifier, such as a unique identifier, for cartridge 200 that can be used by electrospinning unit 100 to adjust process parameters, log use, limit or prevent second use, log other information, and the like.

Mandrel 250 is comprised of end 251 and drive end 252 that pass into receiving holes 221a and 221b of housing 210. End 251 and/or end 252, and/or a cartridge component attached thereto, can function as the rotational element. Drive element 121a and drive element 121b of electrospinning unit 100 engage end 251 and end 252, respectively, such as to rotate mandrel 250 during the electrospinning process. End 251 and/or 252 can have a non-circular surface such as to securely engage on their outer surface drive elements 121a and 121b respectively. Alternatively or additionally, end 251 and/or 252 can include a recess, such as a square, rectangular, hexagonal or elliptical recess to securely engage one or more mating projections of drive elements 121a and/or 121b.

A voltage is applied to mandrel 250, such as a voltage applied to drive end 252 via drive element 121a of electrospinning unit 100. Voltage applied to mandrel 250 can be constant or varying, and is configured to create an electric field sufficient to direct a stream of fiber toward mandrel 250, such as from a polymer delivery assembly and nozzle, both not shown, but described in detail herebelow and integral to electrospinning unit 100, cartridge 200, or both. A voltage is applied to the nozzle that is at a different potential than the voltage applied to mandrel 250, typically creating a voltage potential difference greater than 1000 Volts. Applied voltage can be uniform across the length and circumference of mandrel 250, or it can vary. Applied voltage can be different at a mid portion of mandrel 250 as compared to one or more end portions, such as when a mid portion is at a higher voltage than one or more end portions. Mandrel 250 can be constructed of a conductive material, a resistive or other semi-conductor material, or both. Mandrel 250 can have a different conductivity at one or more portions, such as a mandrel with a different conductivity at a mid portion when compared to an end portion. One or more masks can be included on the surface of mandrel 250, such as an insulating or semi-conductive mask applied to one or both end portions of mandrel 250. The mask can be permanently affixed, or it can be attachable and/or removable.

Mandrel 250 can further comprise conduit 255, tubes 256a and 256b, and fusible link 257. Conduit 255 can be placed over mandrel 250, typically in a relatively centered position. Tubes 256a and 256b are positioned on the ends of conduit 255 on mandrel 250 and provide a relatively uniform diameter profile across mandrel 250. Tubes 256a and 256b can comprise vessel segments, such as portions of the vein used for conduit 255. Tubes 256a and 256b typically have an impedance or electrical permativity similar to conduit 255 such that the potential on the surface of tube 256a, conduit 255, and tube 256b is relatively similar creating a uniform electric field across the length of mandrel 250. Alternatively, tubes 256a and 256b can have an impedance or electrical permativity that is different than conduit 255, such as to create a local electric field that causes a preferential delivery of the polymer. If tubes 256a and 256b are configured to be more insulating than conduit 255, more polymer will be directed onto conduit 255 versus tubes 256a and 256b. If tubes 256a and 256b are configured to be less insulating than conduit 255, more polymer will be delivered away from conduit 255 toward tubes 256a and 256b. Tubes 256a and 256b can have the similar or dissimilar electrical properties. Mandrel 250 can further comprise fusible link 257 that can be used to limit or prevent repeated use in a second graft covering procedure, such by being made an open circuit after first use in electrospinning unit 100, and detectable by electrospinning unit 100 prior to each use.

Housing 210 comprises upper housing 211 and lower housing 212. Upper housing 211 and/or lower housing 212 can be transparent or include one or more transparent portions. These transparent portions allow visible or other light to pass through, such as to allow operation of an optical measurement assembly 160, such as a laser micrometer or a camera such as a high resolution camera. Visualization devices can be used for many purposes, including but not limited to, visualizing the position of a cartridge component and visualization of the polymer stream when directed toward the tubular member holder, mandrel 250. Visualization information can be processed to provide feedback and adjust one or more system parameters in real time.

Ports 201 and 202 are included in the side walls of housing 210 and can provide a connection to an external environmental control device. Ports 201 and 202 can include a covering, such as a removable Tyvek® patch, or can include a resealable membrane. Electrospinning unit 100 can include an environmental control assembly, such as an assembly that maintains temperature, humidity and/or pressure and is attached to one or more of ports 201 and 202 of cartridge 200. Typical environmental control devices include but are not limited to: a positive pressure source; vacuum source; heating unit; cooling unit; humidifier; dehumidifier; and combinations of these. One or more inert gases such as sterilized air or nitrogen can be passed through port 201 and/or port 202.

Housing 210 also includes sensor 280. Sensor 280 can be located in one or more positions of cartridge 200 or electrospinning unit 100, and can comprise multiple sensors. Sensor 280 can be capable of measuring one or more process conditions including but not limited to: temperature; pressure; humidity; an aspect of the solvent or polymer, such as an airborne solvent parameter; velocity (e.g. rotational and translational); diameter; electric field direction or magnitude; a force, such as a force applied to the tubular member holder to create tension; thickness of the applied fiber matrix; and combinations of these. Sensor 280 can be attachable, detachable, or integral to mandrel 250. In some embodiments, sensor 280 is a transducer, such as a light, heat, audio, pressure, magnetic, vibrational, and/or other transducer. Sensor 280 can be used to confirm the integrity of one or more electrical connections, such as an electrical connection to a nozzle or tubular member holder. Sensor 280 can be used to confirm the integrity of one or more mechanical connections, such as a connection maintaining a fluid path between cartridge components.

Slot 226 is located on upper housing 211 such that a polymer fiber can be delivered to cover the outside surface of conduit 255 while an electric field is applied and mandrel 250 is rotated. In typical applications, a nozzle, not shown but included in electrospinning unit 100 and/or cartridge 200, applies a polymer fiber, circumferentially around mandrel 250 along the length of mandrel 250. The polymer fiber stream and/or a polymer delivery nozzle passes through slot 226. Optionally, an electric field guide plate, plate 245 can be attached to upper housing 211 and be electrically attached to jack 247 via wire 246. A power supply, such as a power supply provided by electrospinning unit 100, can be attached to jack 247 and apply a constant or varied voltage to plate 245 to direct and/or modify the direction of a polymer fiber stream toward mandrel 250. Plate 245 is typically flat, concave down or convex down. Plate 245 can be able to move during the electrospinning process, such as via a rotational and/or translational drive assembly, not shown.

System 10 further includes measurement device 160, typically an optical measurement device such as a laser micrometer or camera system. Measurement device 160 can be positioned to view the fiber matrix deposition process including the path of the fiber toward mandrel 250, such as via transparent window 203 of lower housing 212. In some embodiments, the entire construction of lower housing 212 and/or upper housing 211 is transparent.

While electrospinning unit 100 of FIG. 1 shows a single slot 110, multiple slots can be incorporated to process multiple cartridges 200 simultaneously or sequentially.

In the illustrated embodiment, electrospinning unit 100 includes user interface 150 where process parameters can be set and/or adjusted. For example, knob 151 can be used to set the process time, and the time remaining can be viewed on screen 152. Other process parameters include, but are not limited to: mandrel rotation speed; polymer concentration and/or components; mandrel and/or nozzle electrical charge; nozzle translation speed; environmental conditions; and combinations of these.

Figure 2:
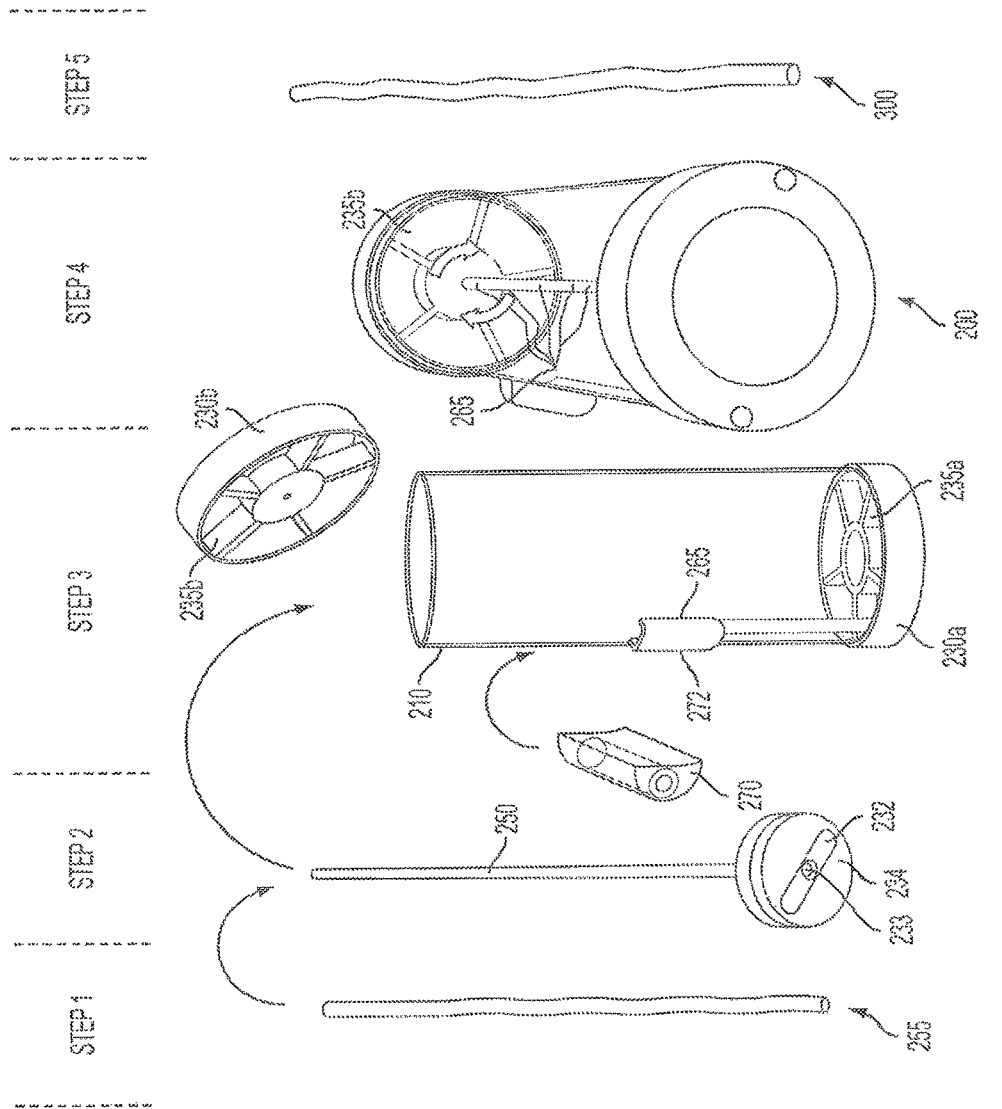
FIG. 2 illustrates a series of steps involved in creating a graft device including a tubular member and a fiber matrix covering, consistent with the current invention.

Referring now to FIG. 2, an example series of steps for assembling a cartridge described herein is illustrated. STEPS 1 through 5 are typically performed using sterile and/or aseptic technique, such as to maintain a processed (fiber matrix covered) tubular member in a sterile state for implantation into a patient. The methods, systems and devices described herein can be configured to avoid contact with non-sterile items or surfaces and/or to provide airtight, watertight or otherwise sterility maintaining barriers. When closed, the cartridge 200 can be sealed. Either doors or removable/penetrable covers (e.g. Tyvek® covers or resealable membranes such as silicone membranes) can be included to protect any openings through which nozzles or ducts would need to communicate with the cartridge 200. During the fiber coating process, conditioned, sterile air can be introduced into the cartridge 200 and maintained at a slightly positive pressure to discourage any ingress of foreign materials from contacting the tubular member.

In STEP 1, a tubular member, conduit 255 is shown. Conduit 255 is typically harvested tissue, such as tissue including but not limited to: vein; artery; lymphatic duct; vas deferens; tear duct; intestine; esophagus; ureter; urethra; trachea; bronchi; duct tissue; Eustachian tube; fallopian tube; and combinations of these (meaning the entire structure or a portion of those tissues). For use in cardiovascular bypass procedures, saphenous vein grafts are typically used. Alternatively or additionally, conduit 255 can include an artificial graft, such as an artificial graft constructed of materials selected form the group consisting of: PFFE; ePTFE; polyester; PVDF-HFP; silicone; polyethylene; polypropylene; polyester based polymer; polyether based polymer; thermoplastic rubber; and combinations of these.

In STEP 2, mandrel 250, a tubular member holder, is shown operably attached to disk 234. Disk 234 includes magnet 232 and conical cup 233. Magnet 232 can be operably connected to an external magnetic drive unit to rotate mandrel 250 and conduit 255, such as during the electrospinning process and/or a quality control step, such as a diameter measurement procedure. Magnet 232 can be a rare earth magnet, for example a neodymium magnet. Conical cup 233 is configured to accept a projection or other protrusion that establishes a rotating connection between the projection and conical cup 233. Conical cup 233 can also be used as an electrical connection between a conductor located on the bottom surface (as oriented in FIG. 2) of disk 234 and a conductor on the top surface of disk 234. In STEP 3, an operator, not shown, slides conduit 255 over mandrel 250 and inserts the assembly into housing 210. Housing 210 has a tubular geometry and mandrel 250 is inserted in the geometric center of the tube. In an alternative embodiment, mandrel 250 can be eccentrically, positioned. Housing 210 includes at one end, attached end cap 230a, with rotatingly mounted fin 235a. End cap 230b is shown ready to be attached to the other end of housing 210 after mandrel 250 has been inserted within housing 210. End cap 230b also can include one or more fins, such as fin 235b. Fins 235a and 235b can be used to create air flow through and/or within housing 210, such as through one or more vents, not shown but preferably included in one or more of end caps 230a and 230b. End cap 230a and/or end cap 230b can be attached to housing 210 via various engaging elements, such as via internal and external threads, press fit or other frictional engagement, bayonet locks, magnetic attachment, and other attachment elements known to those of skill in the art. Alternatively, end cap 230a can be fixedly mounted to housing 210.

End caps 230a and 230b can include active or passive sockets. The term active socket refers to a system that communicates driving forces (e.g., rotation), electrical field, pressure, etc. The term passive socket refers to a system acting as a simple bearing/bushing. The passive components allow rotation and maintain alignment of mandrel 250.

One or both of end caps 230a and 230b can include mechanical rotation elements, such as magnet 232. One or both of end caps 230a and 230b can include electrical connection elements, such as elements that maintain an electrical connection between a rotating object and a stationary object. Rotating electrical connections can include bushings that rotatingly receive a tube, ball bearings, two frictionally engaging surfaces such as slip rings or spring loaded conductive brushes, and the like. Rotating electrical connections can be particularly useful in connecting to a mandrel, nozzle, sensor, conductive surface or other component or assembly of the systems and devices described herein. One or both of end caps 230a and 230b can include one or more filters to allow communication or control of environmental conditions (i.e., ventilation, temperature/humidity control, pressurization, filtration/solvent absorption, and filtration/sterility).

Polymer delivery assembly 270 is the source of polymer material, typically a polymer solution as has been described in detail hereabove. As shown, polymer delivery assembly 270 is ready to be attached to housing 210 at port 272. Port 272 is fluidly attached to nozzle 265. Polymer delivery assembly 270 can include one or more compartments, such as two, three or more discrete compartments including one or more polymers, solvents, agents, or other flowable material. Nozzle 265 can be fixedly mounted to housing 210 or it can be able to translate, oscillate and/or otherwise move relative to mandrel 250 and conduit 255, such as via a lead screw, a rotating head, or other elements described in detail in reference to other figures of this disclosure.

In STEP 4, mandrel 250 and conduit 255 have been inserted within housing 210 and end cap 230b has been attached to an end of housing 210. Polymer delivery assembly 270 has been attached to housing 210. Nozzle 265 and mandrel 250 have been electrically charged, such as via an electrospinning unit, not shown. Mandrel 250 is rotated by a mechanical rotation assembly, not shown, but typically included in the electrospinning unit or another drive assembly and configured to apply a magnetic field to magnet 232 of disk 234 such that disk 234 and mandrel 250 rotate. Fins 235a and 235b are rotated, such as by being mechanically attached to mandrel 250, or another magnetic or other engageable drive mechanism, not shown. Alternatively or additionally, fins can be included outside of housing 210.

In STEP 5, fiber matrix covered graft 300 has been removed from housing 210, and mandrel 250 has been slidingly removed from graft 300. Graft 300 comprises conduit 255 with an electrospun fiber matrix circumferentially surrounding its exterior surface. In some embodiments, cartridge 200 can be reused to process a second tubular member, such as a second harvested graft from the same patient to be implanted in the same surgical procedure, or a second tubular member to be implanted in a different patient in a different surgical procedure.

Figure 3:
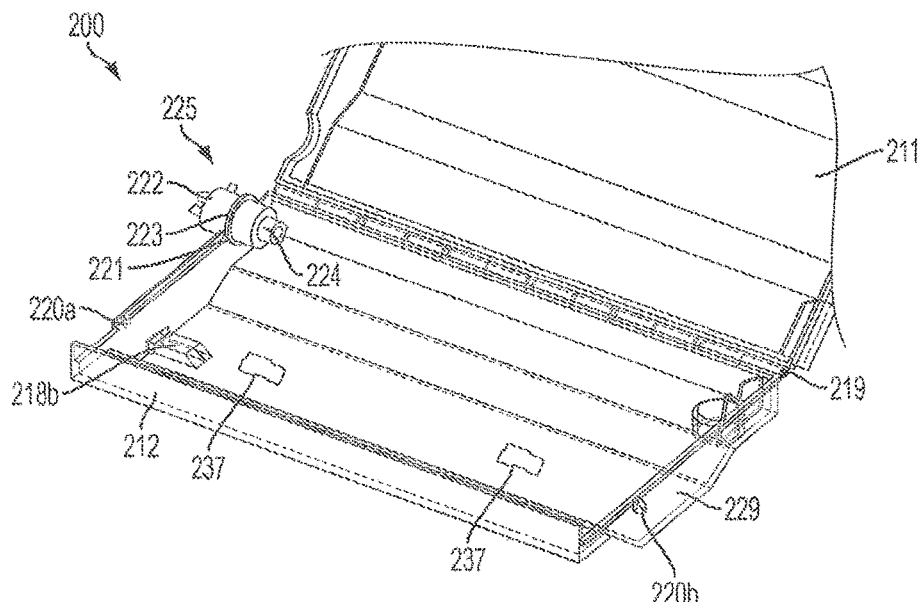
FIG. 3 illustrates a perspective view of a cartridge device, consistent with the present invention.
Figure 4:
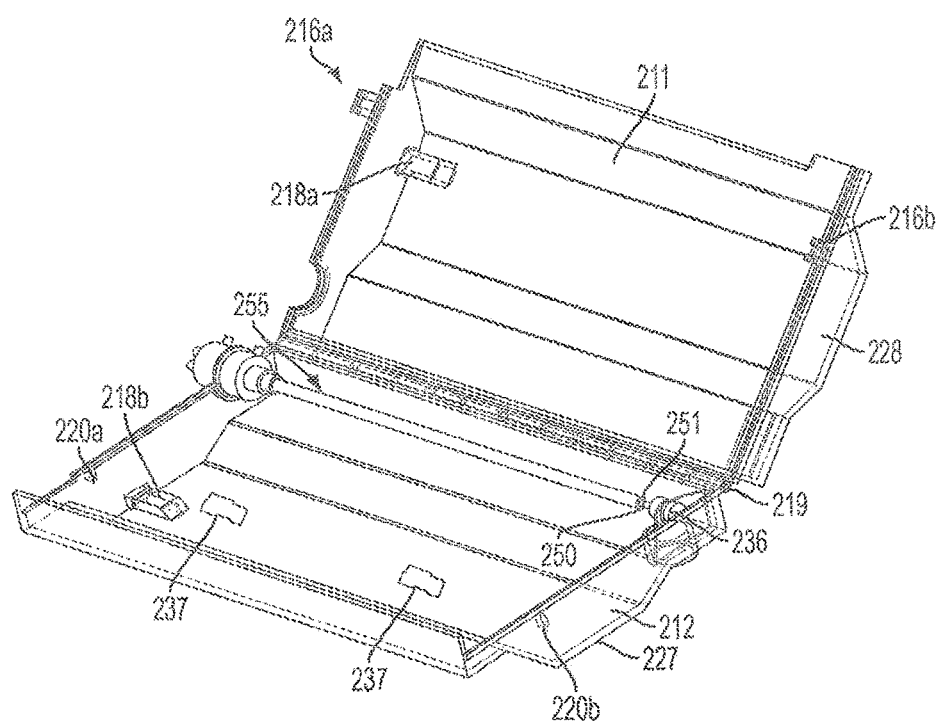
FIG. 4 illustrates a perspective view of the cartridge device of FIG. 3 with a mandrel inserted, consistent with the present invention.

Referring now to FIGS. 3 and 4, a perspective view of an example cartridge device is illustrated. Cartridge 200 is shown as having upper and lower housing portions 211 and 212, respectively, that are rotatably connected via hinge 219. Housing portions 211 and 212 are configured to have an external geometry to enable cartridge 200 to lie flat on a table such as by having at least one flat surface, such as top surface 228 of upper housing 211, or bottom surface 227 of lower housing 212. Two recesses, recess 218a of upper housing 211 and recess 218b of lower housing 212 are placed to align with a mating projection of an electrospinning unit 100 (described below in reference to FIG. 5). A pair of latches comprising snap 216a and 216b which mate with projections 220a and 220b, respectively, engage when upper housing 211 is rotated toward and makes contact with lower housing 212. The internal geometry of housing portions 211 and 212 can be chosen to match the flight path of the fiber being delivered by the electrospinning process. The internal profile of upper housing 211 and lower housing 212 are chosen to be large enough to avoid fibers colliding against the internal walls of the housing, producing webbing on the target. In order to minimize the internal housing size, the flight pattern geometry can be designed to follow (as an external shell) the characteristic geometry of the fiber deposition. The fiber flight path can be controlled by adjusting the electrical field of the electrospinning unit 100, such as by modifying applied voltage or impedance of one or more components. Alternatively or additionally, one or more electric field steering electrodes 237 can be added to attract or repel the fiber during its path to the tubular member holder. Steering electrodes 237 are attached to one or more wires or other conductors, not shown but attached to a power supply, such as a variable power supply.

Cartridge 200 includes rotating coupler 225, a rotational element, comprising, from left to right as shown on the page, first portion 222, seal 223, and second portion 224. Rotating coupler 225 is positioned such that first portion 222 is located outside of lower housing portion 212, second portion 224 is located inside of lower housing portion 212, and seal 223 is located in receiving hole 221. Rotating coupler 225 is also configured to provide an electrical connection from outside of cartridge 200 to its internal chamber, such as to provide a voltage to mandrel 250. Numerous rotating electrical connection types can be used, including but not limited to: two frictionally engaging conductive surfaces such as slip rings, one or more frictionally or compressively engaged ball bearings, a spring loaded brush and ring assembly, and combinations of these. Rotating coupler 225 provides a mechanical link from a rotational drive to mandrel 250 while enabling the cartridge 200 to remain sterile or otherwise remain sealed. Lower housing portion 212 and upper housing 211 can include coating 229, such as to electrically isolate the chamber of cartridge 200 with a Farraday cage effect. Coating 229 is constructed and arranged to create an equipotential surface, such as a surface that is grounded, positively charged or negatively charged. Coating 229 can be maintained at a different voltage than a nozzle configured to deliver the polymer fibers.

Referring specifically to FIG. 4, the cartridge device 200 of FIG. 3 is illustrated with mandrel 250 and bushing 236 inserted into lower housing 212. Mandrel 250 has conduit 255 placed over its outer surface. Additionally, bushing 236 is rotationally engaging end 251 of mandrel 250 and inserted into lower housing 212.

Figure 5:
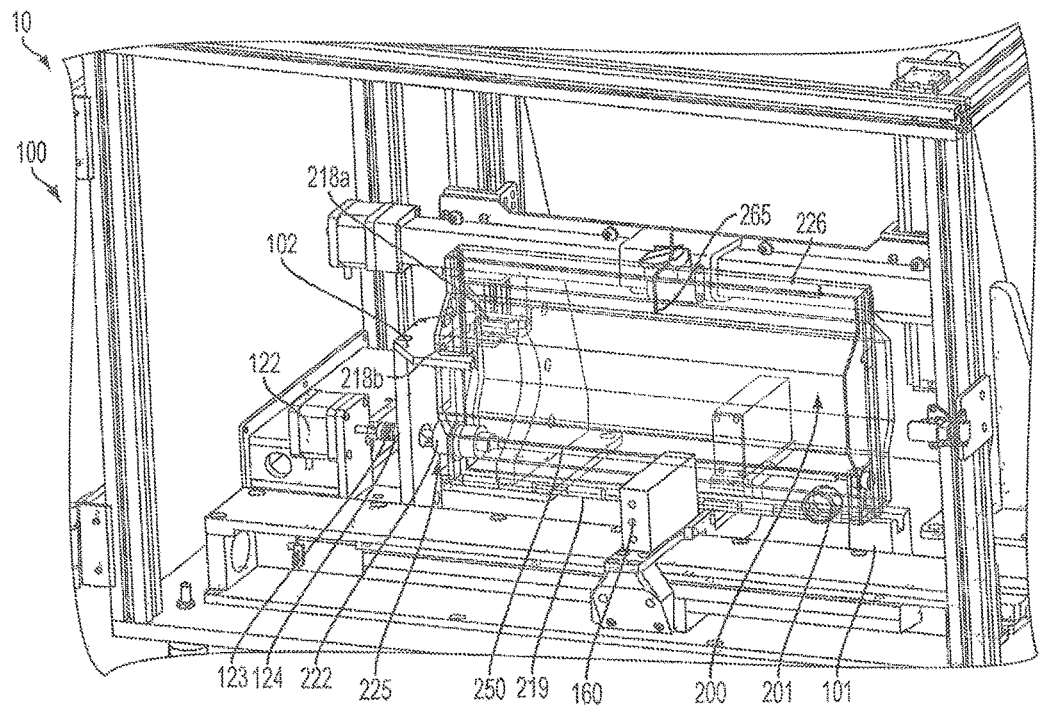
FIG. 5 illustrates a perspective view of a system including an electrospinning unit and an inserted cartridge, consistent with the present invention.

Referring now to FIG. 5, an example system is illustrated. System 10 includes cartridge 200, such as cartridge 200 of FIGS. 3 and 4, which has been inserted into electrospinning unit 100. In some embodiments, electrospinning unit 100 component materials are chosen to electrically isolate all or a portion of cartridge 200. Cartridge 200 is stabilized with fork support 102, which engages recesses 218a and 218b of cartridge 200, drive shaft 124 and bottom support 101. Cartridge 200 is oriented with hinge 219 on the bottom, slot 226 on the top, and rotating coupler 225 on the left (as shown on the page in FIG. 5). Fork support 102 is shown mechanically engaging recesses 218a and 218b of cartridge 200. Coupler 123 is shown mechanically connecting motor 122 to first portion 222 of rotating coupler 225 and configured to rotate mandrel 250 during the fiber deposition process. Coupler 123 can further function as an electrical connection, such as a power or signal connection, to one or more components of cartridge 200, such as a nozzle, a conductive surface, a sensor, a transducer, or other component not shown but described in detail in reference to other drawings included herein.

System 10 can further include optical measurement assembly 160, typically a laser micrometer or high resolution camera that is positioned to measure one or more system, device or process parameters, such as the thickness of the fiber coating deposited on a tubular member positioned mandrel 250 or a characteristic of a flowing fiber stream. Port 201 of cartridge 200 provides access to the internal chamber of cartridge 200 and can be configured to connect to an external environmental control device, not shown, but typically an environmental control device integral to electrospinning unit 100 or a separate device used to control temperature, pressure and/or humidity within cartridge 200. Additional ports can be incorporated, such as uniformly along the length of the sides of cartridge 200, such as to provide even airflow throughout the cartridge 200.

System 10 further includes nozzle 265 which can be integral to cartridge 200 or a component of electrospinning unit 100. Nozzle 265 can be primed prior to, during, and/or after cartridge 200 installation. As described hereabove, nozzle 265 and mandrel 250 are placed at a potential difference (typically greater than 1000V) to facilitate the polymer electrospinning process.

Figure 6:
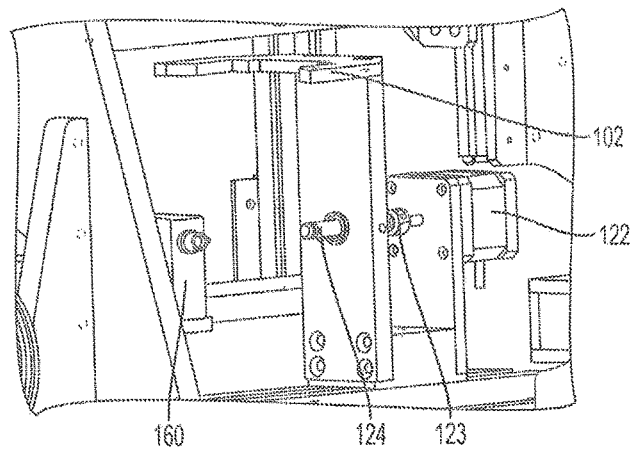
FIG. 6 illustrates a perspective close up view of a drive assembly of the electrospinning unit of FIG. 5, consistent with the present invention.

Referring now to FIG. 6, a close up view of an example attachment and drive assembly is illustrated. Motor 122 is configured to rotate coupler 123 which in turn rotates drive shaft 124. Coupler 123 is configured to electrically isolate drive shaft 124 and motor 122. A set screw, not shown, can be used to clamp an electric field generating power supply wire to coupler 123, which transmits the voltage to drive shaft 124 and onto the mandrel or other tubular member holder of the cartridge device. Fork support 102 engages recesses 218a and 218b of cartridge 200 to prevent motion, cartridge 200 removed for clarity. Optical measurement assembly 160 is configured to measure one or more system, device or process parameters. All of the components can be mounted on a non-conductive plate, not shown, but configured to minimize interference with the electric field between nozzle 265 and mandrel 250 and/or motor function.

Figure 7:
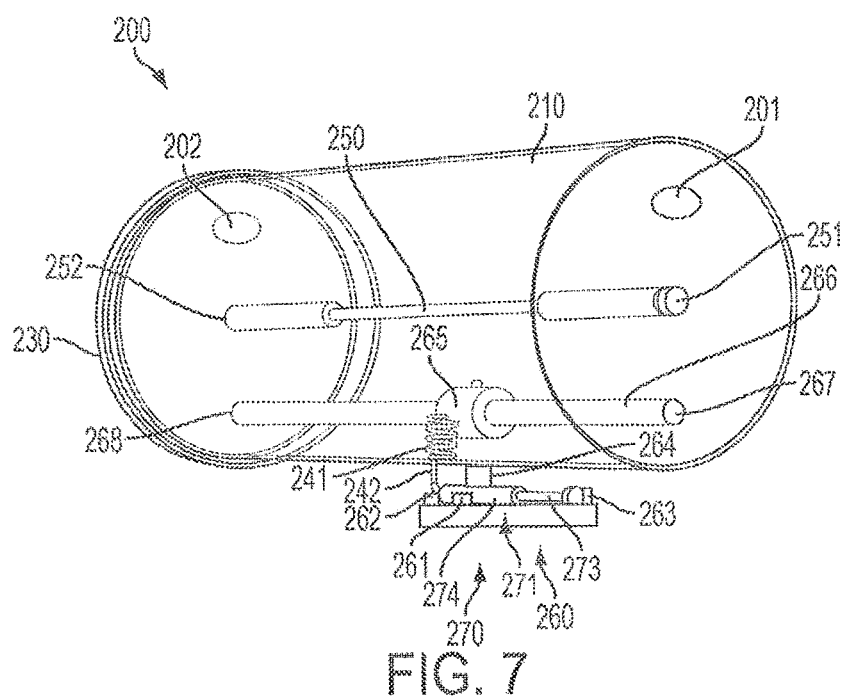
FIG. 7 illustrates a perspective view of a cartridge device with integral polymer delivery assembly, consistent with the present invention.

Referring now to FIG. 7 a perspective view of an example cartridge device is illustrated. Mandrel 250 includes end 251 and drive end 252. Drive end 252 is rotatably attached to end cap 230. Polymer delivery assembly 270 is shown mechanically attached to housing 210 of cartridge 200 by strut 264. Polymer delivery assembly 270 includes syringe 271 comprising plunger 273 and barrel 274. Barrel 274 is removably attached to barrel holder 261 of syringe pump 260, and further maintained in position by end stop 262 (to prevent linear translation during infusion). Polymer delivery assembly 270, or a component thereof, can be configured to be either integral to housing 210 or be attachable and/or removable, such as through attachment via strut 264. Polymer delivery assembly 270 can also have a portion that breaks off during installation or use such as to prohibit undesired reuse. Nozzle 265 is translationally attached to lead screw 266 and configured to translate back and forth between lead screw ends 267 and 268. Nozzle 265 can be attached to numerous forms of linear translation assemblies including but not limited to: a lead screw; a magnetic drive; a belt drive; an oscillating linkage, such as a rotating motor driving a linkage which translates to reciprocating linear motion; and combinations of these. Alternatively or additionally, nozzle 265 can move in a non-linear trajectory, such as a circular trajectory around the mandrel 250, or a circular pattern caused by a rotating drive assembly. Nozzle 265 can be electrically connected, such as through a rotating connector (not shown but described in detail hereabove) and/or additional flexible wiring (also not shown). Nozzle 265 is positioned below mandrel 250. Alternatively nozzle 265 can be positioned above mandrel 250. Preferably, in this instance, nozzle 265 is offset from mandrel 250 such that gravimetric flow of polymer from nozzle 265 will not contact mandrel 250. Syringe 271 is fluidly attached to nozzle 265 through gas removal element 242 and flexible tubing 241, such that linear translation of plunger 273 causes material within syringe 271 to flow to nozzle 265. Gas removal element 242, a typical in-line gas removal component known to those of skill in the art, is configured to remove unwanted gas bubbles from the solvent polymer mixture contained in syringe 271. Flexible tubing 241 is configured to allow motion of the nozzle 265.

In some embodiments, syringe 271 can comprise two or more compartments (not shown, but typically containing different materials such as a polymer and a solvent). In some embodiments, a mixing element, such as an ultrasonic mixing element, can be included, external or integral to polymer delivery assembly 270. A flow pathway configured to mix two fluids, not shown, but connected to the end of barrel 274, can be used to mix one or more components of syringe 271. The flow pathway can include one or more flow deflectors, helical pathways, or other flow disrupting surfaces such as those used in a static or dynamic mixing nozzle common in two part epoxy dispensing systems. Alternative or in addition to syringe pump 260, other pump mechanisms can be incorporated including but not limited to: a peristaltic pump; a positive displacement pump; a magnetohydrodynamic pump; and combinations of these.

Cartridge 200 has two ports 201 and 202 which can be independently configured to function as inlet or outlet ports. Ports 201 and 202 can be attached to an external environmental control device, a source of pressure or vacuum, and can include a filter, such as a 0.2 micron filter. A membrane can cover ports 201 and/or 202, such as a Tyvek® membrane used to maintain sterility prior to use, and or a resealable membrane such as a resealable silicone membrane.

External environmental control devices can be integral to an electrospinning unit 100 or separate, and are typically selected from the group consisting of: positive pressure source; vacuum source; heating unit; cooling unit; humidifier; dehumidifier; ionizing unit, and combinations of these. Ports 201 and/or 202 can include a plenum or other gas dispersing device, such as to distribute sterile air, nitrogen or other gas substantially evenly along the length of the tubular member. Ports 201 and/or 202 can be used to maintain one or more conditions inside cartridge 200, including but not limited to, temperature, humidity and pressure. In some embodiments, ports 201 and/or 202 are used to control the partial pressure of a solvent that is mixed with a polymer and delivered to cartridge 200.

Figure 8:
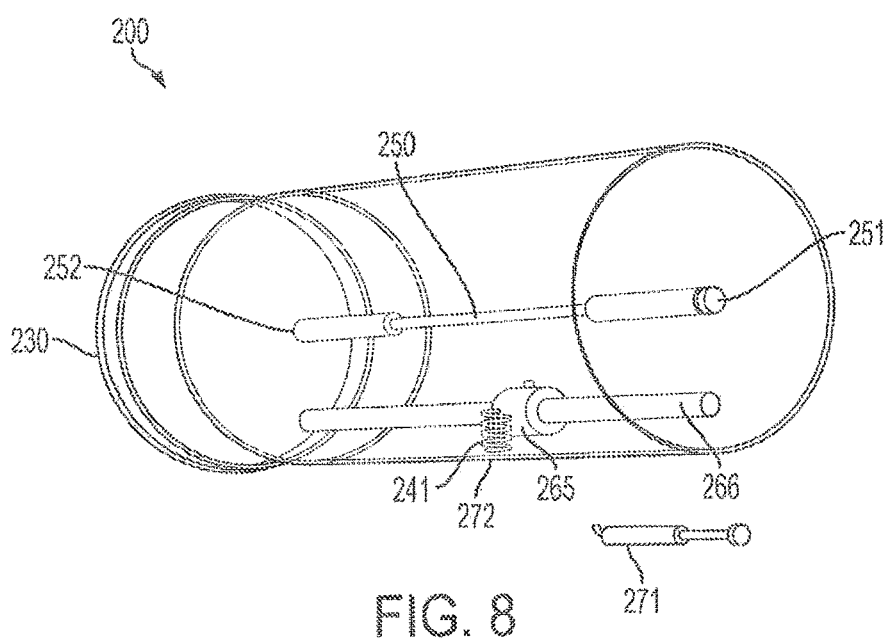
FIG. 8 illustrates a perspective view of a cartridge device with an attachable polymer delivery assembly, consistent with the present invention.

Referring now to FIG. 8, another example cartridge device is illustrated. Cartridge 200 of FIG. 8 is similar to cartridge 200 of FIG. 7; however syringe 271 is separate and attachable to housing 210. Syringe 271 can be fluidly and/or mechanically connected to cartridge 200 through port 272. In some embodiments, syringe 271 has sufficient polymer solvent mixture to enable multiple grafts to be fiber coated before depletion, for example to coat multiple veins during a multiple bypass procedure.

Figure 9:
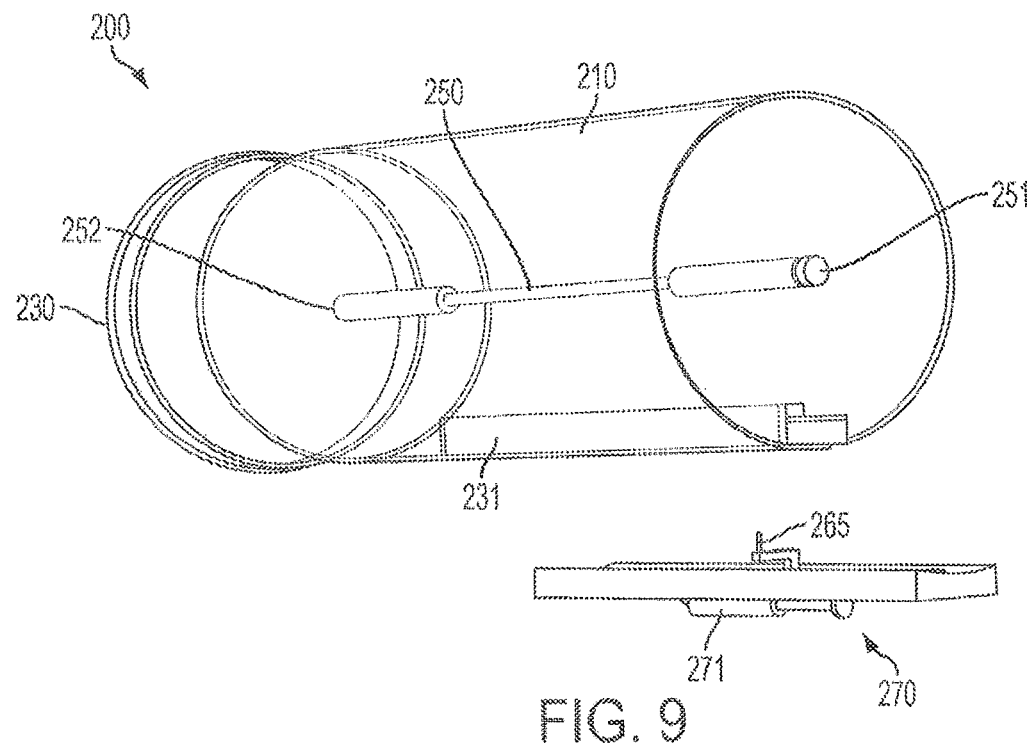
FIG. 9 illustrates a perspective view of a cartridge device with an attachable polymer delivery assembly and nozzle, consistent with the present invention.
Figure 10:
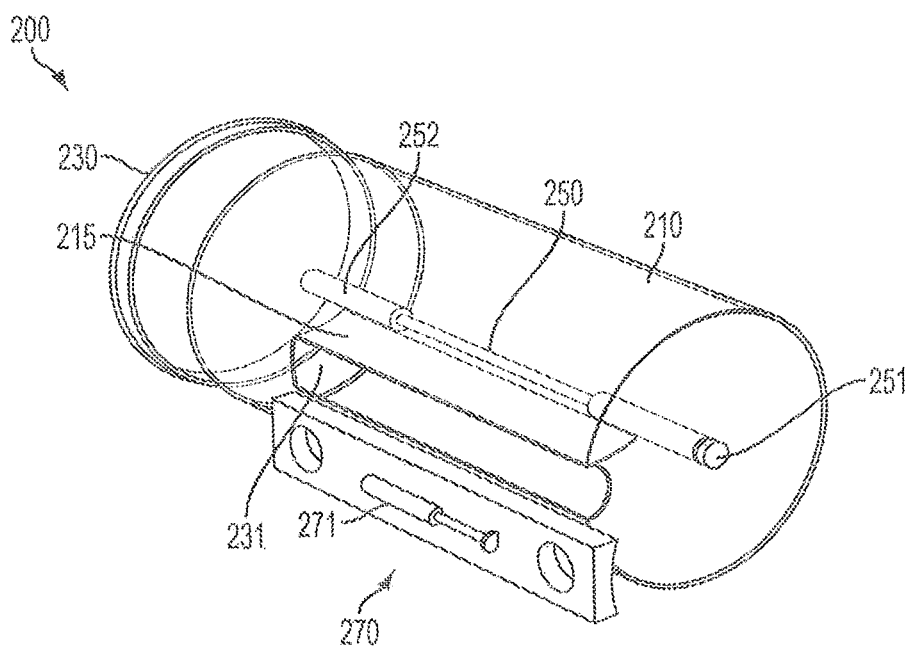
FIG. 10 illustrates another perspective view of the cartridge device of FIG. 9, consistent with the present invention.

Referring now to FIGS. 9 and 10, two perspective views of an example cartridge are illustrated. Cartridge 200 includes polymer delivery assembly 270. Assembly 270 includes syringe 271 and integrated nozzle 265. Nozzle 265 is positioned to be inserted into housing 210 through slot 231. Polymer delivery assembly 270 is configured to seal against housing 210, such as to create a sterile barrier seal. Alternatively, polymer delivery assembly could have multiple nozzles, such as to reduce electrospinning time. Housing 210 includes door 215 covering slot 231. Door 215 can be configured to open upon insertion of nozzle 265. Alternatively, door 215 could be a seal, such as a paper seal that could be configured to be broken upon insertion of nozzle 265, or a resealable membrane. Cartridge 200 can include one or more sensors, such as to monitor temperature, humidity, pressure, electric field, all not shown but described in detail hereabove.

Figure 11:
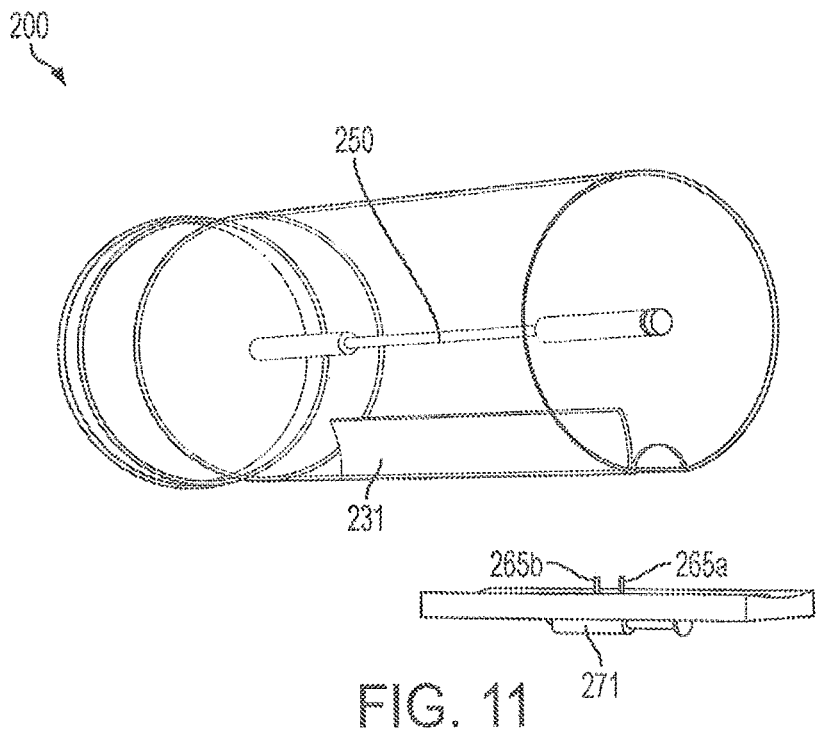
FIG. 11 illustrates a perspective view of a cartridge device with an attachable polymer delivery assembly and dual nozzles, consistent with the present invention.

Referring now to FIG. 11, a perspective view of another example cartridge device is illustrated. Cartridge 200 comprises two fixed nozzles 265a and 265b which can be configured to deliver polymer fiber sequentially or simultaneously, such as to reduce fiber deposition processing time. Nozzles 265a and 265b can be attached to a single source of polymer fiber material or to two similar or dissimilar sources of polymer fiber material.

Figure 12:
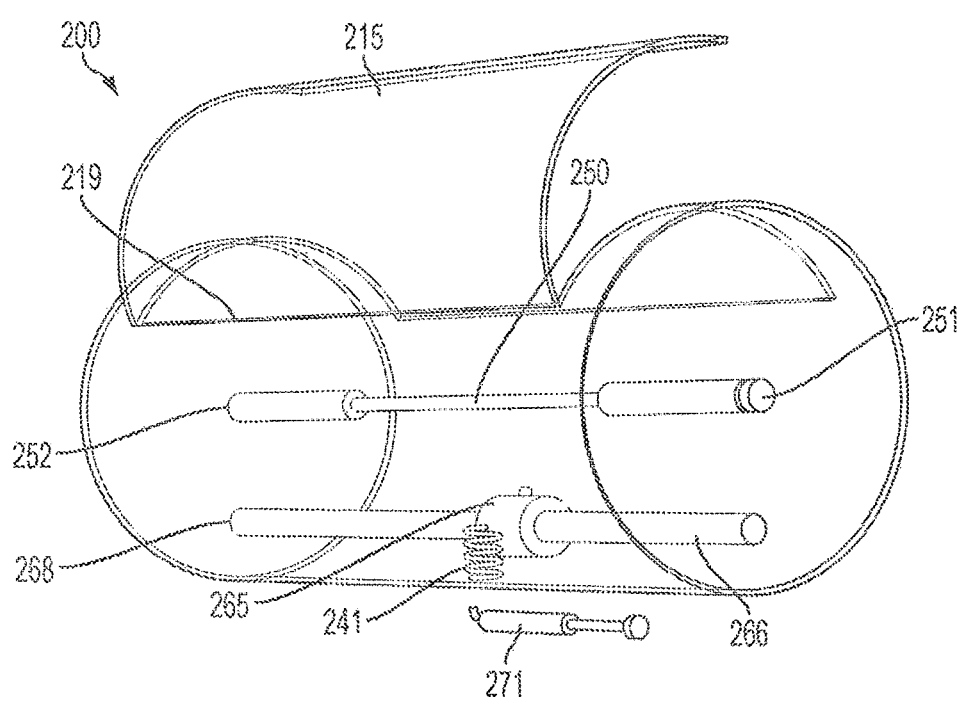
FIG. 12 illustrates a perspective view of a cartridge device with an access door, consistent with the present invention.

Referring now to FIG. 12, a perspective view of another cartridge device is illustrated. Cartridge 200 comprises door 215 rotatably connected to housing 210 with hinge 219, and sized to allow mandrel 250 to be placed within cartridge 200. Cartridge 200 can be configured to be sterilized, used to process a first tubular member, and then re-sterilized for repeated use. The associated electrospinning unit can be maintained in a sterile field, adjacent to the patient. Both the inside and outside of cartridge 200 remain sterile during processing.

Figure 13:
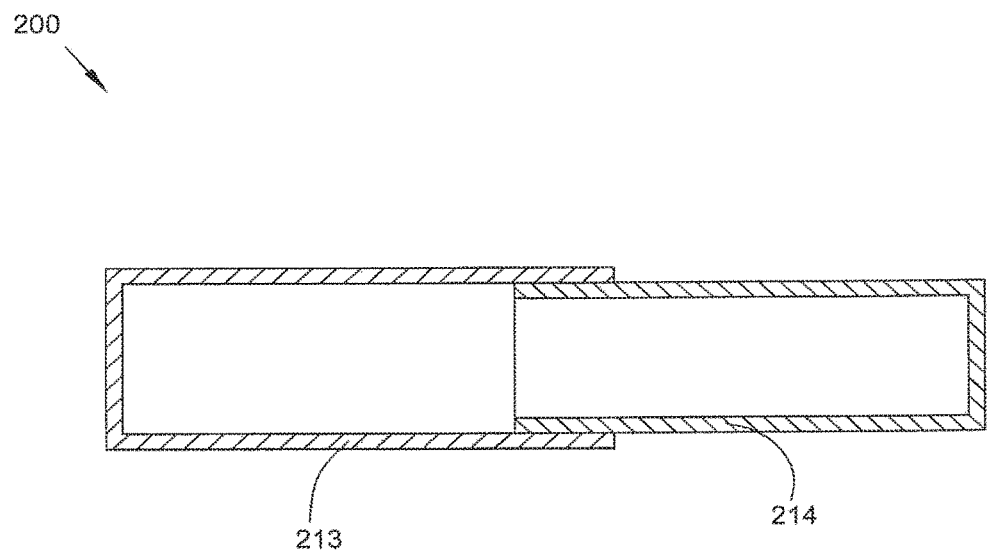
FIG. 13 illustrates a side sectional view of an expandable cartridge device, consistent with the present invention.

Referring now to FIG. 13, a side sectional view of a cartridge device is illustrated. Cartridge 200 comprises first and second housing portions, 213 and 214 respectively, which slide relative to each other enabling cartridge 200 to both expand and contract longitudinally. Cartridge 200 can be used to adjust to multiple tubular member holder (e.g. mandrel) lengths.

Figure 14:
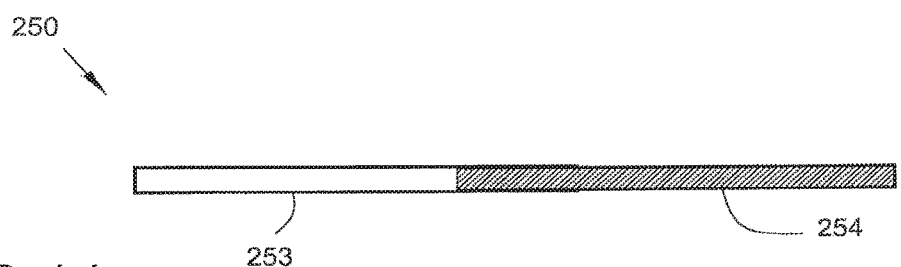
FIG. 14 illustrates a side sectional view of an expandable mandrel, consistent with the present invention.

Referring now to FIG. 14, a side sectional view of a tubular member holder device is illustrated. Mandrel 250 comprises first and second mandrel portions 253 and 254, respectively, that slide relative to each other enabling mandrel 250 to both expand and contract longitudinally. Mandrel 250 can be used to adjust to multiple conduit lengths, such as multiple saphenous vein graft lengths.

The cartridge housings described herein can assume numerous geometries, such as a tubular housings, rectangular housings, and trapezoidal housings. The housings can include multiple portions, such as upper and lower portions, and can include components such as hinges, doors, slots and other openings. Cartridges can include one or more sensors or transducers. In some embodiments, one or more nozzles are integral to the cartridge, such as at a side or bottom location to prevent gravitational dripping of any substance from the nozzle onto the tubular member. Alternatively or additionally, one or more nozzles can be integral to the electrospinning unit of the systems described herein, similarly placed at any location into the cartridge, such as through a slot or door. While the tubular member holder described herein has been described in detail as a rotatable mandrel, other tubular member holders can be employed, rotating and fixed, such as to accommodate other forms of tissue such as nerve tissue, tendon tissue, ligament tissue, organ and other non-linear tissues, and other tissues.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it can be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A cartridge device for applying a fiber matrix to a tubular member, the cartridge device comprising:
   a housing that defines a chamber and comprises an attachment port;
   a tubular member holder positioned within the chamber;
   a rotation element operably connected to the tubular member holder;
   a polymer delivery assembly configured to deliver the fiber matrix comprising at least one polymer onto the tubular member;
   an inlet port; and
   an outlet port,
   wherein the attachment port is configured to (i) fluidly attach to a polymer reservoir comprising the at least one polymer and (ii) provide the at least one polymer to the polymer delivery assembly, and wherein at least one of the inlet port or the outlet port comprises a filtered port.

2. The device according to claim 1, wherein the inlet port, the outlet port, or a combination thereof comprises a membrane, wherein the membrane covers an opening of the inlet port, the outlet port, or the combination thereof.

3. The device according to claim 2, wherein the membrane is removably attached to the opening of the inlet port, the outlet port, or the combination thereof.

4. The device according to claim 2, wherein the membrane is configured to be punctured to uncover the opening of the inlet port, the outlet port, or the combination thereof.

5. The device according to claim 2, wherein the membrane comprises a resealable membrane.

6. The device according to claim 1, wherein the filtered port is configured to maintain sterility of the tubular member holder.

7. The device according to claim 1, wherein the filtered port is configured to provide ventilation of the housing.

8. The device according to claim 1, wherein the filtered port comprises a 0.2 micron filter.

9. The device according to claim 1, wherein the housing comprises a first portion, a mating second portion, and a seal therebetween.

10. The device according to claim 9, wherein the seal comprises a sterility barrier.

11. The device according to claim 1, wherein the polymer delivery assembly is configured to deliver a solvent, and wherein the device is configured to control a partial pressure of the solvent.

12. The device according to claim 11, wherein at least one of the inlet port or the outlet port attaches to an external environmental control device.

13. The device according to claim 12, wherein the external environmental control device is selected from the group consisting of: a positive pressure source; a vacuum source; a heating unit; a cooling unit; a humidifier; a dehumidifier; an ionizing unit; and any combination thereof.

14. The device according to claim 1, wherein the inlet port provides an inert gas to the device and controls one or more of: an ambient pressure, a humidity, or a combination thereof within the device.

15. The device according to claim 14, wherein the inert gas comprises nitrogen.

16. The device according to claim 1, wherein the polymer delivery assembly further comprises a nozzle configured to deliver the fiber matrix onto the tubular member.

17. The device according to claim 16, wherein the nozzle is positioned at a top of the housing or at a bottom of the housing.

18. The device according to claim 16, wherein the nozzle moves in a manner selected from the group consisting of: translation; oscillation; rotation; and any combination thereof.

19. The device according to claim 1, wherein the tubular member comprises a harvested tissue.

20. The device according to claim 19, wherein the tubular member comprises the harvested tissue selected from the group consisting of: a vein; an artery; a lymphatic duct; a vas deferens; a tear duct; an intestine; an esophagus; a ureter; a urethra; a trachea; a bronchi; a duct tissue; an Eustachian tube; a fallopian tube; and any combination thereof.

* * * * *